United States Patent
Brandes

(10) Patent No.: US 9,907,797 B2
(45) Date of Patent: Mar. 6, 2018

(54) COMBINATION THERAPIES FOR OVERCOMING RESISTANCE TO MITOTIC AGENTS DURING CHEMOTHERAPY

(71) Applicant: EMORY UNIVERSITY, Atlanta, GA (US)

(72) Inventor: Johann C Brandes, Atlanta, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 14/877,203

(22) Filed: Oct. 7, 2015

(65) Prior Publication Data

US 2016/0095859 A1   Apr. 7, 2016

Related U.S. Application Data

(60) Provisional application No. 62/060,854, filed on Oct. 7, 2014.

(51) Int. Cl.
| | | |
|---|---|---|
| A61K 31/513 | (2006.01) | |
| A61K 31/337 | (2006.01) | |
| A61K 45/06 | (2006.01) | |

(52) U.S. Cl.
CPC .......... *A61K 31/513* (2013.01); *A61K 31/337* (2013.01); *A61K 45/06* (2013.01)

(58) Field of Classification Search
CPC .............. A61K 2300/00; A61K 31/337; A61K 31/513; A61K 45/06
See application file for complete search history.

(56) References Cited

U.S. PATENT DOCUMENTS

| | | |
|---|---|---|
| 2004/0180889 A1 | 9/2004 | Suto |
| 2005/0049267 A1 | 3/2005 | Suto |
| 2009/0163545 A1 | 6/2009 | Goldfarb |

FOREIGN PATENT DOCUMENTS

| | | |
|---|---|---|
| JP | 11-258732 | 9/1999 |
| KR | 100965726 | 6/2010 |

OTHER PUBLICATIONS

Wolff, Manfred E. "Burger's Medicinal Chemistry, 5ed, Part I", John Wiley & Sons, 1995, pp. 975-977.*
Anderson (Chem and Biol 10:787-797, 2003).*
Thiel (Nature Biotechnol 2:513-519, 2004).*
Banker, G.S. et al, "Modern Pharmaceutics, 3ed.", Marcel Dekker, New York, 1996, pp. 451 and 596.*
Brandes et al. "CHFR promoter hypermethylation in colon cancer correlates with the microsatellite instability phenotype" Carcinogenesis, 2005; 26(6): 1152-1156.
Brodie et al. "Molecular characteristics of non-small cell lung cancer with reduced CHFR expression in The Cancer Genome Atlas (TCGA) project" Respir Med., 2015; 109(1): 131-136.

(Continued)

*Primary Examiner* — Savitha M Rao
(74) *Attorney, Agent, or Firm* — Emory Patent Group

(57) ABSTRACT

This disclosure relates to the uses of compounds that target an interaction between CHFR and PARP1. In certain embodiments, the disclosure relate to treating cancer by administering a mitotic inhibitor such as a taxane and a vinca alkaloid in combination with a compound that inhibits CHFR and PARP1 interactions, such as 5-((1-benzyl-1H-indol-3-yl)methylene)-1-(3,4-dimethylphenyl)pyrimidine-2,4,6(1H,3H,5H)-trione, derivatives or salts thereof, optionally in further combination with a third anti-cancer agent.

9 Claims, 22 Drawing Sheets

(56) References Cited

OTHER PUBLICATIONS

Brodie et al. "Small molecule inhibition of the CHFR-PARP1 interaction as novel approach to overcome intrinsic taxane resistance in cancer" Oncotarget, 2015; 6(31): 30773-30786.

Choi et al. "Discovery of the inhibitors of tumor necrosis factor alpha with structure-based virtual screening" Bioorganic & Medicinal Chemistry Letters, 2010; 20: 6195-6198.

Hong et al. "Identification of new Hsp90 inhibitors by structure-based virtual screening" Bioorganic & Medicinal Chemistry Letters, 2009; 19: 4839-4842.

Kashima et al. "CHFR Protein Regulates Mitotic Checkpoint by Targeting PARP-1 Protein for Ubiquitination and Degradation" The Journal of Biological Chemistry, 2012; 287: 12975-12984.

Khadka et al. "Barbiturates as Noncompetitive Inhibitors of PTP1B and Competitive Inhibitors of Vaccinia H1-Related (VHR)" Phosphatase, 2011; 32(8): 2883-2884.

Kouskoumvekaki et al. "Discovery of a Novel Selective PPARγ Ligand with Partial Agonist Binding Properties by Integrated in Silico/in Vitro Work Flow" J. Chem. Inf. Model., 2013; 53: 923-937.

Park et al. "Structure-based virtual screening approach to identify novel classes of PTP1B inhibitors" European Journal of Medicinal Chemistry, 2009; 44: 3280-3284.

Pelosof et al. "CHFR silencing or microsatellite instability is associated with increased antitumor activity of docetaxe or gemcitabine in colorectal cancer" Int J Cancer., 2014; 34(3): 596-605.

Pillai et al. "CHFR protein expression predicts outcomes to taxane-based first line therapy in metastatic NSCLC" Clin Cancer Res., 2013; 19(6): 1603-1611.

Satoh et al. "Epigenetic inactivation of CHFR and sensitivity to microtubule inhibitors in gastric cancer" Cancer Res., 2003; 63(24): 8606-8613.

Wang et al. "CHFR suppression by hypermethylation sensitizes endometrial cancer cells to paclitaxel." Int J Gynecol Cancer, 2011; 21: 996-1003.

Yu et al. "Chfr is required for tumor suppression and Aurora A regulation" Nat Genet., 2005; 37(4): 401-406.

\* cited by examiner

COMBINATION THERAPIES FOR OVERCOMING RESISTANCE TO MITOTIC AGENTS DURING CHEMOTHERAPY

CROSS REFERENCE TO RELATED APPLICATION

This application claims priority to U.S. Provisional Application No. 62/060,854 filed Oct. 7, 2014, hereby incorporated by reference in its entirety.

GOVERNMENT SUPPORT

This invention was made with government support under 7-IK2BX001283-03 awarded by the Veterans' Health Administration. The government has certain rights in the invention.

BACKGROUND

Microtubular-targeted chemotherapy agents such as taxanes are among the most widely prescribed first- and second-line chemotherapy choices for patients with the most common malignancies including lung-, breast-, and prostate cancer. Unfortunately, primary resistance to taxanes is a common clinical problem. Thus, there is a need to find improved chemotherapy treatments.

Checkpoint with forkhead and ringfinger domains (CHFR) function to delay cell cycle entry into metaphase in response to mitotic stress. Cells that are deficient in this gene undergo apoptosis. CHFR has an N-terminal forkhead domain, a RING domain which functions as an E3-ubiqutin ligase, and a cysteine-rich C terminal domain, which mediates interactions with other proteins. Yu et al. report CHFR is required for tumor suppression and Aurora A regulation. See Nature genetics, 2005, 37:401-406. C-terminal region of CHFR has a poly-ADP ribose binding zinc-finger (PBZ) motif which mediates a protein-protein interaction with PARP1. See Kashima et al., J Biol Chem, 2012, 287:12975-12984.

Satoh et al. report epigenetic inactivation of (CHFR) and sensitivity to microtubule inhibitors in gastric cancer. Cancer research, 2003, 63:8606-8613. Methylation of CHFR is reported to be associated with sensitivity to chemotherapy agents. See Pelosof et al., Int J Cancer, 2014, 134:596-605; Brandes et al., Carcinogenesis, 2005, 26:1152-1156; and Wang et al., Int J Gynecol Cancer, 2011, 21:996-1003. Pillai et al. report CHFR protein expression predicts outcomes to taxane-based first line therapy in metastatic NSCLC. See Clinical cancer research: an official journal of the American Association for Cancer Research, 2013, 19:1603-1611.

Kouskoumvekaki et al. report selective PPARγ ligands with partial agonist binding properties by integrated in silico/in vitro work flow. J Chem Inf Model, 2013, 53(4): 923-37. See also KR 2009053504, JP 11258732, US 2004/0180889, US 2005/0049267, and US 2009/0163545.

References cited herein are not an admission of prior art.

SUMMARY

This disclosure relates to the use of compounds that target an interaction between CHFR and PARP1. In certain embodiments, the disclosure relates of methods of treating cancer by the pharmacologic inhibition of the CHFR-PARP1 interaction. In certain embodiments, the disclosure relate to treating cancer by administering a mitotic inhibitor such as a taxane and/or a vinca alkaloid in combination with a compound that inhibits CHFR and PARP1 interactions, such as 5-((1-benzyl-1H-indol-3-yl)methylene)-1-(3,4-dimethylphenyl)pyrimidine-2,4,6(1H,3H,5H)-trione, derivatives or salts thereof, optionally in further combination with a third anti-cancer agent.

In certain embodiments, the disclosure relates to formulations and pharmaceutical compositions comprising a pharmaceutically acceptable excipient and a compound comprising Formula I,

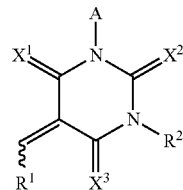

Formula I salts, esters, prodrugs, or derivatives thereof wherein A, $R^1$, $R^2$, $X^2$, and $X^3$ are reported herein.

In certain embodiments, the composition is in the form of a pill, tablet, capsule, or aqueous buffer solution. In certain embodiments, the buffer comprises an agent selected from ethanol, maleic acid, tartaric acid, lactic acid, citric acid, acetic acid, sodium bicarbonate, sodium phosphate, dextrin, saccharide, polysaccharide, cyclodextrin, β-cyclodextrin, 2-hydroxypropyl-β-cyclodextrin, γ-cyclodextrin, sulfobutylether-β-cyclodextrin, macrogol-15-hydroxystearate, dimethylacetamide, propylene glycol, polyethylene glycol, polysorbates and polyoxyl castor oil.

In certain embodiments, the disclosure relates to methods of treating cancer comprising administering an effective amount of a compound disclosed herein in combination with a mitotic inhibitor. In certain embodiments, the mitotic inhibitor is selected from a taxane, paclitaxel, paclitaxel bonded to albumin, paclitaxel linked to docosahexaenoic acid, paclitaxel bonded to a polyglutamate, EMC-Arg-Ser-Ser-Tyr-Tyr-Ser-Leu-PABC-paclitaxel [EMC: ε-maleimidocaproyl; PABC: p-aminobenzyloxycarbonyl], paclitaxel conjugated to poly(ethylene glycol)-b-poly(acrylic acid), docetaxel, a vinca alkaloid, vinblastine, vincristine, vindesine, vinorelbine, and combinations thereof.

In certain embodiments, the method further comprises administering a third anti-cancer agent such as gefitinib, erlotinib, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and lenalidomide.

In certain embodiments, the cancer is selected from breast cancer, pancreatic cancer, ovarian cancer, colon cancer, gastric cancer, lung cancer, non-small cell lung cancer (NSCLC), small cell lung cancer (SCLC), skin cancer, melanoma, prostate cancer, head cancer, neck cancer, renal cancer, throat cancer, hepatic cancer, brain cancer, glioblastoma, leukemia, and lymphoma.

BRIEF DESCRIPTION OF THE FIGURES

FIG. 1I shows data indicating a mutation in the RING domain (CHFR-ΔR-PBZ*) leads to protein levels comparable to those of wt-CHFR, indicating that auto-ubiquitination and -degradation of CHFR are responsible for the low expression of CHFR-PBZ*EV, empty vector; PBZ*, PBZ mutated CHFR; ΔR, Ring domain mutated CHFR.

DETAILED DISCUSSION

Figure 1A:
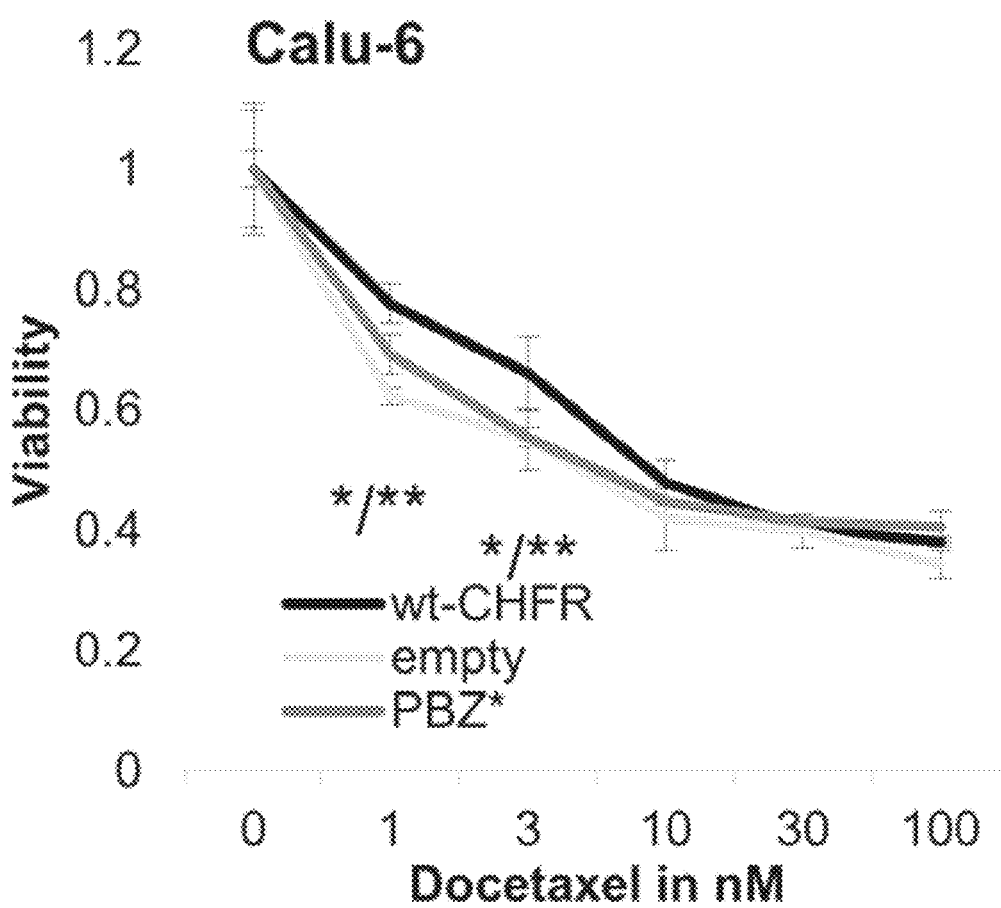
FIG. 1A shows data where pDEST40-wt-CHFR, pDEST40-CHFR-PBZ* (mutated PBZ domain) and empty pDEST40 vector were transfected into CHFR deficient Calu-6 NSCLC cells. The effect of Docetaxel after 72 hours was established by XTT assay. Stable transfection of wt-CHFR increases taxane resistance over empty vector and over CHFR-PBZ* (*$p<0.05$ for CHFR-wt vs empty vector; **$p<0.05$ for CHFR-wt vs CHFR-PBZ).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

In certain embodiments, a pharmaceutical agent, which may be in the form of a salt or prodrug, is administered in methods disclosed herein that is specified by a weight. This refers to the weight of the recited compound. If in the form of a salt or prodrug, then the weight is the molar equivalent of the corresponding salt or prodrug.

It must be noted that, as used in the specification and the appended claims, the singular forms "a," "an," and "the" include plural referents unless the context clearly dictates otherwise.

As used herein, "alkyl" means a noncyclic straight chain or branched, unsaturated or saturated hydrocarbon such as those containing from 1 to 10 carbon atoms, while the term "lower alkyl" or "$C_{1-4}$alkyl" has the same meaning as alkyl but contains from 1 to 4 carbon atoms. The term "higher alkyl" has the same meaning as alkyl but contains from 7 to 20 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Aryl" means an aromatic carbocyclic monocyclic or polycyclic ring such as phenyl or naphthyl. Polycyclic ring systems may, but are not required to, contain one or more non-aromatic rings, as long as one of the rings is aromatic.

As used herein, "heteroaryl" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—CH3).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—CH3).

"Alkanoyl" refers to an alkyl as defined above with the indicated number of carbon atoms attached through a carbonyl bride (i.e., —(C=O)alkyl).

"Alkylsulfonyl" refers to an alkyl as defined above with the indicated number of carbon atoms attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfonamide" refers to an alkyl as defined above with the indicated number of carbon atoms attached through a sulfamoyl bridge (i.e., —NHS(=O)$_2$alkyl), and an "Arylsulfonamide" refers to an alkyl attached through a sulfamoyl bridge (i.e., —NHS(=O)$_2$aryl).

"Alkylsulfinyl" refers to an alkyl as defined above with the indicated number of carbon atoms attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)ORb, —NR$_a$SO$_2$R$_b$, —C(=O)R$_a$, —C(=O)OR$_a$, —C(=O)NR$_a$R$_b$, —OC(=O)NR$_a$Rb, —OR$_a$, —SR$_a$, —SOR$_a$, —S(=O)$_2$R$_a$, —OS(=O)$_2$R$_a$ and —S(=O)$_2$ORa. R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

As used herein, "salts" refer to derivatives of the disclosed compounds where the parent compound is modified making acid or base salts thereof. Examples of salts include, but are not limited to, mineral or organic acid salts of basic residues such as amines, alkylamines, or dialkylamines; alkali or organic salts of acidic residues such as carboxylic acids; and the like. In preferred embodiment the salts are conventional nontoxic pharmaceutically acceptable salts including the quaternary ammonium salts of the parent compound formed, and non-toxic inorganic or organic acids. Preferred salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Subject" refers any animal, preferably a human patient, livestock, or domestic pet.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis.

As used herein, the terms "prevent" and "preventing" include the prevention of the recurrence, spread or onset. It is not intended that the present disclosure be limited to complete prevention. In some embodiments, the onset is delayed, or the severity of the disease is reduced.

As used herein, the terms "treat" and "treating" are not limited to the case where the subject (e.g. patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

As used herein, the term "derivative" refers to a structurally similar compound that retains sufficient functional attributes of the identified analogue. The derivative may be structurally similar because it is lacking one or more atoms, substituted, a salt, in different hydration/oxidation states, or because one or more atoms within the molecule are switched, such as, but not limited to, replacing a oxygen atom with a sulfur atom or replacing an amino group with a hydroxyl group. The derivative may be a prodrug. Derivatives may be prepare by any variety of synthetic methods or appropriate adaptations presented in synthetic or organic chemistry text books, such as those provide in March's Advanced Organic Chemistry: Reactions, Mechanisms, and Structure, Wiley, 6th Edition (2007) Michael B. Smith or Domino Reactions in Organic Synthesis, Wiley (2006) Lutz F. Tietze hereby incorporated by reference.

"Cancer" refers any of various cellular diseases with malignant neoplasms characterized by the proliferation of cells. It is not intended that the diseased cells must actually invade surrounding tissue and metastasize to new body sites. Cancer can involve any tissue of the body and have many different forms in each body area. Within the context of certain embodiments, whether "cancer is reduced" can be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It can also be identified by a change in relevant biomarker or gene expression profile, such as PSA for prostate cancer, HER2 for breast cancer, or others.

Methods of Use

It has been discovered that an interaction between CHFR and PARP1 stabilizes CHFR protein levels. Although it is not intended that any embodiments of this disclosure are to be limited by any particular mechanism, it is believed that the interaction is mediated by PBZ domain of CHFR and that disruption leads to auto-ubiquitination and subsequent proteasomal degradation of CHFR. Reduced CHFR expression in lung cancer is associated with improved survival. Taxane sensitivity is increased in gastric, colon, and cervical cancers in which CHFR is silenced epigenetically. It is contemplated that pharmacologic inhibition of the CHFR-PARP1 interaction with subsequent loss of CHFR and disruption of antephase checkpoint function helps to overcome taxane resistance across a wide spectrum of different tumor types.

Thus, in certain embodiments, the disclosure relates to methods of treating cancer comprising administering an effective amount of a compound that inhibits the CHFR-PARP1 interaction in combination with a taxane or other mitotic inhibitor. In certain embodiment, the mitotic inhibitor is selected from a taxane, paclitaxel, paclitaxel bonded to albumin, docetaxel, a vinca alkaloid, vinblastine, vincristine, vindesine, vinorelbine, and combinations thereof.

Several experiments indicate that the compound A3 (FIG. 3C) inhibits the mitotic checkpoint by targeting the interaction between CHFR and PARP1. A3 treatment leads to the functional disruption of the docetaxel-induced mitotic checkpoint, a point in the cell cycle in which the CHFR-PARP1 interaction is greatest. A3 synergizes with docetaxel in CHFR expressing cell lines. A3 administration results in a pharmacodynamic reduction in CHFR expression in vivo in human tumor xenograft models. Unlike A3, the PARP1 inhibitor ABT-888 is not capable of disrupting the interaction between CHFR and PARP1. This is surprising since the enzymatically inactive PARP1-E988K mutant does not interact with CHFR.

In certain embodiments, the subject is diagnosed with, exhibiting symptoms of, or at risk of cancer. In certain embodiments, the cancer is selected from breast cancer, pancreatic cancer, ovarian cancer, colon cancer, gastric cancer, lung cancer, non-small cell lung cancer (NSCLC), small cell lung cancer (SCLC), melanoma, skin cancer, prostate cancer, head cancer, neck cancer, renal cancer, throat cancer, hepatic cancer, leukemia, or lymphoma. In certain embodiments, the cancer is endometrial cancer, cervical cancer, testicular cancer, or Kaposi's sarcoma.

In certain embodiments, the disclosure relates to methods of treating or preventing actinic keratosis, psoriasis, squamous cell carcinoma or basal cell carcinoma.

In certain embodiments, the administration is topical to an area of skin or cancer exposed on the skin. In certain embodiments, the subject diagnosed with, exhibiting symptoms of, or at risk of actinic keratosis, psoriasis, squamous cell carcinoma or basal cell carcinoma.

In certain embodiments, the cancer is a hematological malignancy, a leukemia, lymphoma, acute lymphoblastic leukemia (ALL), acute myelogenous leukemia (AML), chronic lymphocytic leukemia (CLL), small lymphocytic lymphoma (SLL), chronic myelogenous leukemia, acute monocytic leukemia (AMOL), Hodgkin's lymphomas, non-Hodgkin's lymphomas, Burkitt lymphoma, B-cell lymphoma, or multiple myelomacervical.

In certain embodiments, cancer therapeutic strategies entail pharmaceutical compositions comprising a mitotic inhibitor administered in combination with compound inhibitor of the CHFR-PARP1 interaction and a third or multiple anti-cancer agents such as gefitinib, erlotinib, cisplatin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and/or lenalidomide or combinations thereof.

The cancer treatments disclosed herein can be applied as a sole therapy or can involve, conventional surgery or radiotherapy or chemotherapy. Such chemotherapy can include one or more of the following categories of anti-cancer agents:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulfan and nitrosoureas); antimetabolites (for example antifolates such as fluoropyrimidines like 5-fluorouracil and gemcitabine, tegafur, raltitrexed, methotrexate, cytosine arabinoside and hydroxyurea); anti-tumor antibiotics (for example anthracyclines like adriamycin, bleomycin, doxorubicin, daunomycin, epirubicin, idarubicin, mitomycin-C, dactinomycin and mithramycin); and topoisomerase inhibitors (for example epipodophyllotoxins like etoposide and teniposide, amsacrine, topotecan and camptothecin); and proteosome inhibitors (for example bortezomib [Velcade®]); and the agent anegrilide [Agrylin®]; and the agent alpha-interferon;

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-Her2 antibody trastuzumab and the anti-epidermal growth factor receptor (EGFR) antibody, cetuximab), farnesyl transferase inhibitors, tyrosine kinase inhibitors and serine/threonine kinase inhibitors, for example inhibitors of the epidermal growth factor family for example EGFR family tyrosine kinase inhibitors such as: N-(3-chloro-4-fluorophenyl)-7-methoxy-6-(3-morpholinopropoxy)quinazolin-4-amine (gefitinib), N-(3-ethynylphenyl)-6,7-bis(2-methoxyethoxy)quinazolin-4-amine (erlotinib), and 6-acrylamido-N-(3-chloro-4-fluorophenyl)-7-(3-morpholinopropoxy)quinazolin-4-amine (CI 1033), for example inhibitors of the platelet-derived growth factor family and for example inhibitors of the hepatocyte growth factor family, for example inhibitors of phosphotidylinositol 3-kinase (PI3K) and for example inhibitors of mitogen activated protein kinase kinase (MEK½) and for example inhibitors of protein kinase B (PKB/Akt), for example inhibitors of Src tyrosine kinase family and/or Abelson (AbI) tyrosine kinase family such as dasatinib (BMS-354825) and imatinib mesylate (Gleevec™); and any agents that modify STAT signalling;

(v) antiangiogenic agents such as those which inhibit the effects of vascular endothelial growth factor, (for example the anti-vascular endothelial cell growth factor antibody bevacizumab [Avastin™]) and compounds that work by other mechanisms (for example linomide, inhibitors of integrin ocvβ3 function and angiostatin);

(vi) vascular damaging agents such as Combretastatin A4;

(vii) antisense therapies, for example those which are directed to the targets listed above, such as an anti-RAS antisense; and (viii) immunotherapy approaches, including for example ex-vivo and in-vivo approaches to increase the immunogenicity of subject tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies, and approaches using the immunomodulatory drugs thalidomide and lenalidomide [Revlimid®].

A chronic lymphocytic leukemia (CLL) chemotherapy regiment may include chlorambucil or cyclophosphamide, plus a corticosteroid such as prednisone or prednisolone. Alternative treatments with nucleoside drugs such as fludarabine, pentostatin, or cladribine may be utilized. Patients may undergo an allogeneic or autologous bone marrow transplantation. In certain embodiments, the disclosure contemplates combination treatments using a mitotic inhibitor administered in combination with compound inhibitor of the CHFR-PARP1 interaction and further with chloroambucil, cyclophosphamide, prednisone, prednisolone, fludarabine, pentostatin, and/or cladribine or combinations thereof.

An acute lymphoblastic leukemia chemotherapy regiment may include prednisone, vincristine, and an anthracycline drug, L-asparaginase or cyclophosphamide. Other options include prednisone, L-asparaginase, and vincristine. Other treatments may include antimetabolite drugs such as methotrexate and 6-mercaptopurine (6-MP). In certain embodiments, the disclosure contemplates combination treatments using a compound inhibitor of the CHFR-PARP1 interaction in combination with COP, CHOP, R-CHOP, imatinib, alemtuzumab, vincristine, L-asparaginase or cyclophosphamide, methotrexate and/or 6-mercaptopurine (6-MP). COP refers to a chemotherapy regimen used in the treatment of lymphoma of cyclophosphamide, vincristine, and prednisone or prednisolone and optionally hydroxydaunorubicin (CHOP) and optionally rituximab (R-CHOP).

In certain embodiments, the disclosure relates to the treatment of any cancer reported herein comprising administering a compound inhibitor of the CHFR-PARP1 interaction and paclitaxel and/or a platinum based agent such as carboplatin.

In certain embodiments, the disclosure relates to the treatment of breast cancer comprising administering a mitotic inhibitor administered in combination with compound inhibitor of the CHFR-PARP1 interaction and an aromatase inhibitor, e.g. anastrozole or letrozole.

In certain embodiments, the disclosure relates to the treatment of breast cancer comprising administering a mitotic inhibitor administered in combination with compound inhibitor of the CHFR-PARP1 interaction and cyclophosphamide, doxorubicin, docetaxel, or combinations thereof In certain embodiments, the disclosure relates to the treatment of breast cancer comprising administering a mitotic inhibitor administered in combination with compound inhibitor of the CHFR-PARP1 interaction and cyclophosphamide, methotrexate, fluorouracil, or combinations thereof.

In certain embodiments, the disclosure relates to the treatment of breast cancer comprising administering a mitotic inhibitor administered in combination with compound inhibitor of the CHFR-PARP1 interaction and a monoclonal antibody to HER2, e.g., trastuzumab.

In certain embodiments, the disclosure relates to the treatment of pancreatic cancer comprising administering a mitotic inhibitor administered in combination with compound inhibitor of the CHFR-PARP1 interaction and gemcitabine.

In certain embodiments, the disclosure relates to the treatment of pancreatic cancer comprising administering a mitotic inhibitor administered in combination with compound inhibitor of the CHFR-PARP1 interaction and erlotinib.

In certain embodiments, the disclosure relates to the treatment of breast, lung, or pancreatic cancer comprising administering a compound inhibitor of the CHFR-PARP1 interaction and paclitaxel or paclitaxel bonded to albumin.

In certain embodiments, the disclosure relates to the treatment of pancreatic cancer comprising administering a mitotic inhibitor administered in combination with compound inhibitor of the CHFR-PARP1 interaction and erlotinib, gemcitabine, or combinations.

In certain embodiments, the disclosure relates to the treatment of pancreatic cancer comprising administering a mitotic inhibitor administered in combination with compound inhibitor of the CHFR-PARP1 interaction and folinic acid, fluorouracil, irinotecan, or combinations thereof.

In certain embodiments, the disclosure relates to the treatment of head and/or neck cancer comprising administering compound inhibitor of the CHFR-PARP1 interaction and docetaxel optionally in combination with cisplatin and/or fluorouracil.

In certain embodiments, the disclosure relates to the treatment of hepatic cancer comprising administering a mitotic inhibitor administered in combination with compound inhibitor of the CHFR-PARP1 interaction and lipiodol.

In certain embodiments, the disclosure relates to the treatment of renal, hepatic, or thyroid cancer comprising administering a mitotic inhibitor administered in combination with compound inhibitor of the CHFR-PARP1 interaction and sorafenib.

In certain embodiments, the disclosure relates to the treatment of hepatic cancer comprising administering a mitotic inhibitor administered in combination with compound inhibitor of the CHFR-PARP1 interaction and doxorubicin.

Compounds

In certain embodiments, a compound inhibitor of the CHFR-PARP1 interaction for uses reported herein is A3, 5-((1-benzyl-1H-indol-3-yl)methylene)-1-(3,4-dimethylphenyl)pyrimidine-2,4,6(1H,3H,5H)-trione, derivatives or salts thereof. In certain embodiments, the derivatives are 5-((1-methyl-1H-indol-3-yl)methylene)-1-phenylpyrimidine-2,4,6(1H,3H,5H)-trione substituted with one or more, the same or different substituents. In certain embodiments, the derivatives are 5-((1-methyl-1H-indol-3-yl)methylene)pyrimidine-2,4,6(1H,3H,5H)-trione substituted with one or more, the same or different substituents.

In certain embodiments, contemplated compounds have Formula I.

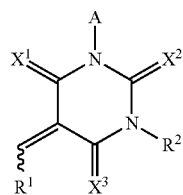

Formula I salts, esters, prodrugs, or derivatives thereof wherein,

A is a carbocyclyl, aryl, or heterocyclyl, wherein A is optionally substituted with one or more, the same or different, $R^{20}$;

$X^1$, $X^2$, and $X^3$ are each O or S;

$R^1$ is a heterocyclyl or a nitrogen containing five membered heterocyclic ring wherein the nitrogen is substituted with benzyl wherein $R^1$ is optionally substituted with one or more, the same or different, $R^{20}$;

$R^2$ is hydrogen, alkyl, amino, formyl, carboxy, carbamoyl, alkylamino, (alkyl)$_2$amino, alkylsulfinyl, alkylsulfonyl, arylsulfonyl, carbocyclyl, aryl, or heterocyclyl, wherein $R^2$ is optionally substituted with one or more, the same or different, $R^{20}$;

$R^{20}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, $R^2$ is hydrogen or alkyl.

In certain embodiments, the compound of Formula I has Formula IA,

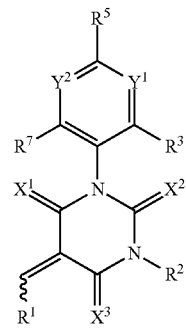

Formula IA $X^1$, $X^2$, and $X^3$ are each O or S;

$Y^1$ is C—$R^4$, $Y^2$ is $CR^6$ $R^1$ is a heterocyclyl comprising a nitrogen containing five membered ring wherein the nitrogen is substituted with benzyl wherein $R^1$ is optionally substituted with one or more, the same or different, $R^{20}$;

$R^2$ is hydrogen;

$R^3$ is hydrogen, alkyl, halogen, nitro, cyano, hydroxy, amino, mercapto, formyl, carboxy, carbamoyl, alkoxy, alkylthio, or alkylamino;

$R^4$ is hydrogen, alkyl, halogen, nitro, cyano, hydroxy, amino, mercapto, formyl, carboxy, carbamoyl, alkoxy, alkylthio, or alkylamino;

$R^5$ is methyl wherein $R^5$ is optionally substituted with one or more, the same or different, $R^{20}$;

$R^6$ is hydrogen, alkyl, halogen, nitro, cyano, hydroxy, amino, mercapto, formyl, carboxy, carbamoyl, alkoxy, alkylthio, or alkylamino;

$R^7$ is hydrogen, alkyl, halogen, nitro, cyano, hydroxy, amino, mercapto, formyl, carboxy, carbamoyl, alkoxy, alkylthio, or alkylamino;

$R^{20}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, the compound of Formula I has Formula IB,

Formula IB

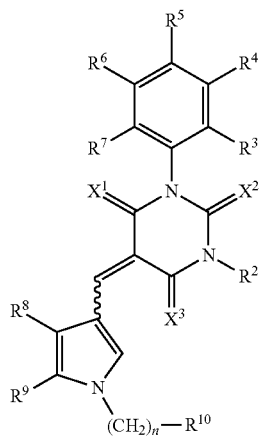

X$^1$, X$^2$, and X$^3$ are each O or S;
n is 1, 2, or 3;
R$^2$ is hydrogen;
R$^3$ is hydrogen, alkyl, halogen, nitro, cyano, hydroxy, amino, mercapto, formyl, carboxy, carbamoyl, alkoxy, alkylthio, or alkylamino;
R$^4$ and R$^5$ are each individually and independently is hydrogen, alkyl, halogen, nitro, cyano, hydroxy, amino, mercapto, formyl, carboxy, carbamoyl, alkoxy, alkylthio, or alkylamino;
R$^6$ is hydrogen, alkyl, halogen, nitro, cyano, hydroxy, amino, mercapto, formyl, carboxy, carbamoyl, alkoxy, alkylthio, or alkylamino;
R$^7$ is hydrogen, alkyl, halogen, nitro, cyano, hydroxy, amino, mercapto, formyl, carboxy, carbamoyl, alkoxy, alkylthio, or alkylamino;
R$^8$ and R$^9$ are hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^8$ and R$^9$ are optionally substituted with one or more, the same or different, R$^{20}$; or R$^8$ and R$^9$ with attached atoms come together to form a carbocyclyl, aryl, or heterocyclyl optionally substituted with one or more, the same or different, R$^{20}$;
R$^{10}$ is carbocyclyl, aryl, or heterocyclyl, wherein R$^{10}$ is optionally substituted with one or more, the same or different, R$^{20}$;
R$^{20}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{20}$ is optionally substituted with one or more, the same or different, R$^{21}$; and
R$^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, at least one of R$^5$ and W are methyl optionally substituted with one or more, the same or different, R$^{20}$.

In certain embodiments, the compound of Formula I has Formula IC,

Formula IC

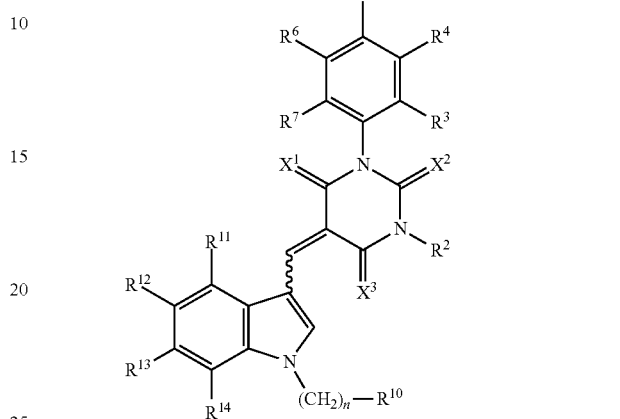

X$^1$, X$^2$, and X$^3$ are each O or S;
n is 1, 2, or 3;
R$^2$ is hydrogen;
R$^3$ is hydrogen, alkyl, halogen, nitro, cyano, hydroxy, amino, mercapto, formyl, carboxy, carbamoyl, alkoxy, alkylthio, or alkylamino;
R$^4$ and R$^5$ are each individually and independently is hydrogen, alkyl, halogen, nitro, cyano, hydroxy, amino, mercapto, formyl, carboxy, carbamoyl, alkoxy, alkylthio, or alkylamino provided that at least one of R$^5$ and R$^4$ are methyl optionally substituted with one or more, the same or different, R$^{20}$;
R$^6$ is hydrogen, alkyl, halogen, nitro, cyano, hydroxy, amino, mercapto, formyl, carboxy, carbamoyl, alkoxy, alkylthio, or alkylamino;
R$^7$ is hydrogen, alkyl, halogen, nitro, cyano, hydroxy, amino, mercapto, formyl, carboxy, carbamoyl, alkoxy, alkylthio, or alkylamino;
R$^{10}$ is carbocyclyl, aryl, or heterocyclyl, wherein R$^{10}$ is optionally substituted with one or more, the same or different, R$^{20}$;
R$^{11}$, R$^{12}$, R$^{13}$, and R$^{14}$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{11}$, R$^{12}$, R$^{13}$, an R$^{14}$ are optionally substituted with one or more, the same or different, R$^{20}$;
R$^{20}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein R$^{20}$ is optionally substituted with one or more, the same or different, R$^{21}$; and
R$^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, compound of Formula I has Formula ID,

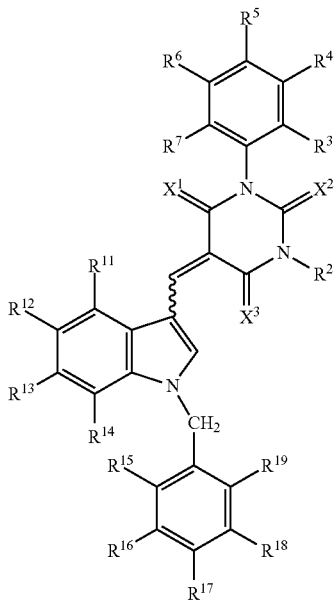

Formula ID $X^1$, $X^2$, and $X^3$ are each O or S;

$R^2$ is hydrogen;

$R^3$ is hydrogen, alkyl, halogen, nitro, cyano, hydroxy, amino, mercapto, formyl, carboxy, carbamoyl, alkoxy, alkylthio, or alkylamino;

$R^4$ and $R^5$ are each individually and independently is hydrogen, alkyl, halogen, nitro, cyano, hydroxy, amino, mercapto, formyl, carboxy, carbamoyl, alkoxy, alkylthio, or alkylamino provided that at least one of $R^5$ and $R^4$ are methyl optionally substituted with one or more, the same or different, $R^{20}$;

$R^6$ is hydrogen, alkyl, halogen, nitro, cyano, hydroxy, amino, mercapto, formyl, carboxy, carbamoyl, alkoxy, alkylthio, or alkylamino;

$R^7$ is hydrogen, alkyl, halogen, nitro, cyano, hydroxy, amino, mercapto, formyl, carboxy, carbamoyl, alkoxy, alkylthio, or alkylamino;

$R^{11}$, $R^{12}$, $R^{13}$, $R^{14}$, $R^{15}$, $R^{16}$, $R^{17}$, $R^{18}$, and $R^{19}$ are each individually and independently hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{11}$, $R^{12}$, $R^{13}$, $R^{14}$, $R^{15}$, $R^{16}$, $R^{17}$, $R^{18}$, and $R^{19}$ are optionally substituted with one or more, the same or different, $R^{20}$; and $R^{20}$ is alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, wherein $R^{20}$ is optionally substituted with one or more, the same or different, $R^{21}$; and $R^{21}$ is halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

With regard to any of the embodiments disclosed herein, $R^4$ is methyl.

With regard to any of the embodiments disclosed herein, $R^5$ is methyl.

With regard to any of the embodiments disclosed herein, $R^4$ and $R^5$ are methyl.

In certain embodiments, $X^1$, $X^2$, and $X^3$ are oxygen.

Formulations

Pharmaceutical compositions disclosed herein can be in the form of pharmaceutically acceptable salts, as generally described below. Typically the pharmaceutical product is in the form of a tablet, pill, capsule, or buffered aqueous solution such a phosphate buffer containing a saccharide or polysaccharide. Some preferred, but non-limiting examples of suitable pharmaceutically acceptable organic and/or inorganic acids are hydrochloric acid, hydrobromic acid, sulfuric acid, nitric acid, acetic acid and citric acid, as well as other pharmaceutically acceptable acids known per se (for which reference is made to the references referred to below).

When the compounds of the disclosure contain an acidic group as well as a basic group, the compounds of the disclosure can also form internal salts, and such compounds are within the scope of the disclosure. When a compound contains a hydrogen-donating heteroatom (e.g. NH), salts are contemplated to cover isomers formed by transfer of the hydrogen atom to a basic group or atom within the molecule.

Pharmaceutically acceptable salts of the compounds include the acid addition and base salts thereof. Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases can also be formed, for example, hemisulphate and hemicalcium salts. For a review on suitable salts, see Handbook of Pharmaceutical Salts: Properties, Selection, and Use by Stahl and Wermuth (Wiley-VCH, 2002), incorporated herein by reference.

The compounds described herein can be administered in the form of prodrugs. A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds. Examples of structuring a compound as prodrugs can be found in the book of Testa and Caner, Hydrolysis in Drug and Prodrug Metabolism, Wiley (2006) hereby incorporated by reference. Typical prodrugs form the active metabolite by transformation of the prodrug by hydrolytic enzymes, the hydrolysis of amides, lactams, peptides, carboxylic acid esters, epoxides or the cleavage of esters of inorganic acids.

Pharmaceutical compositions typically comprise an effective amount of a compound and a suitable pharmaceutical acceptable carrier. The preparations can be prepared in a manner known per se, which usually involves mixing the at least one compound according to the disclosure with the one or more pharmaceutically acceptable carriers, and, if desired, in combination with other pharmaceutical active compounds, when necessary under aseptic conditions. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences. It is well known that ester prodrugs are readily degraded in the body to release the corresponding alcohol. See e.g., Imai, Drug Metab Pharmacokinet. (2006) 21(3):173-85, entitled "Human carboxylesterase isozymes: catalytic properties and rational drug design."

Generally, for pharmaceutical use, the compounds can be formulated as a pharmaceutical preparation comprising at least one compound and at least one pharmaceutically acceptable carrier, diluent or excipient and/or adjuvant, and optionally one or more further pharmaceutically active compounds.

The pharmaceutical preparations of the disclosure are preferably in a unit dosage form, and can be suitably packaged, for example in a box, blister, vial, bottle, sachet, ampoule or in any other suitable single-dose or multi-dose holder or container (which can be properly labeled); optionally with one or more leaflets containing product information and/or instructions for use. Generally, such unit dosages will contain between 1 and 1000 mg, and usually between 5 and 500 mg, of the at least one compound of the disclosure e.g., about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used. The compound will generally be administered in an "effective amount," by which it is meant any amount of a compound that, upon suitable administration, is sufficient to achieve the desired therapeutic or prophylactic effect in the subject to which it is administered. Usually, depending on the condition to be prevented or treated and the route of administration, such an effective amount will usually be between 0.01 to 1000 mg per kilogram body weight of the patient per day, more often between 0.1 and 500 mg, such as between 1 and 250 mg, for example about 5, 10, 20, 50, 100, 150, 200 or 250 mg, per kilogram body weight of the patient per day, which can be administered as a single daily dose, divided over one or more daily doses. The amount(s) to be administered, the route of administration and the further treatment regimen can be determined by the treating clinician, depending on factors such as the age, gender and general condition of the patient and the nature and severity of the disease/symptoms to be treated. Reference is made to U.S. Pat. Nos. 6,372,778, 6,369,086, 6,369,087 and 6,372,733 and the further references mentioned above, as well as to the standard handbooks, such as the latest edition of Remington's Pharmaceutical Sciences.

Formulations containing one or more of the compounds described herein can be prepared using a pharmaceutically acceptable carrier composed of materials that are considered safe and effective and can be administered to an individual without causing undesirable biological side effects or unwanted interactions. The carrier is all components present in the pharmaceutical formulation other than the active ingredient or ingredients. As generally used herein "carrier" includes, but is not limited to, diluents, binders, lubricants, disintegrators, fillers, pH modifying agents, preservatives, antioxidants, solubility enhancers, and coating compositions.

Carrier also includes all components of the coating composition which can include plasticizers, pigments, colorants, stabilizing agents, and glidants. Delayed release, extended release, and/or pulsatile release dosage formulations can be prepared as described in standard references such as "Pharmaceutical dosage form tablets," eds. Liberman et. al. (New York, Marcel Dekker, Inc., 1989), "Remington—The science and practice of pharmacy," 20th ed., Lippincott Williams & Wilkins, Baltimore, Md., 2000, and "Pharmaceutical dosage forms and drug delivery systems," 6th Edition, Ansel et al., (Media, Pa.: Williams and Wilkins, 1995). These references provide information on carriers, materials, equipment and process for preparing tablets and capsules and delayed release dosage forms of tablets, capsules, and granules.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Additionally, the coating material can contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-beta-alanine, sodium N-lauryl-beta-iminodipropionate, myristoamphoacetate, lauryl betaine and lauryl sulfobetaine.

If desired, the tablets, beads, granules, or particles can also contain minor amount of nontoxic auxiliary substances such as wetting or emulsifying agents, dyes, pH buffering agents, or preservatives.

The compositions described herein can be formulation for modified or controlled release. Examples of controlled release dosage forms include extended release dosage forms, delayed release dosage forms, pulsatile release dosage forms, and combinations thereof.

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, a reservoir and a matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

In certain preferred embodiments, the plastic material is a pharmaceutically acceptable acrylic polymer, including but not limited to, acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly (methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers. Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename Eudragit®. In further preferred embodiments, the acrylic polymer comprises a mixture of two acrylic resin lacquers commercially available from Rohm Pharma under the tradenames Eudragit® RL30D and Eudragit® RS30D, respectively. Eudragit® RL30D and Eudragit® RS30D are copolymers of acrylic and methacrylic esters with a low content of quaternary ammonium groups, the molar ratio of ammonium groups to the remaining neutral (meth)acrylic esters being 1:20 in Eudragit® RL30D and 1:40 in Eudragit® RS30D. The mean molecular weight is about 150,000. Edragit® S-100 and Eudragit® L-100 are also preferred. The code designations RL (high permeability) and RS (low permeability) refer to the permeability properties of these agents. Eudragit® RL/RS mixtures are insoluble in water and in digestive fluids. However, multiparticulate systems formed to include the same are swellable and permeable in aqueous solutions and digestive fluids.

The polymers described above such as Eudragit® RL/RS can be mixed together in any desired ratio in order to ultimately obtain a sustained-release formulation having a desirable dissolution profile. Desirable sustained-release multiparticulate systems can be obtained, for instance, from 100% Eudragit® RL, 50% Eudragit® RL and 50% Eudragit® RS, and 10% Eudragit® RL and 90% Eudragit® RS. One skilled in the art will recognize that other acrylic polymers can also be used, such as, for example, Eudragit® L.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above can be combined in a final dosage form comprising single or multiple units. Examples of multiple units include, but are not limited to, multilayer tablets and capsules containing tablets, beads, or granules. An immediate release portion can be added to the extended release system by means of either applying an immediate release layer on top of the extended release core using a coating or compression process or in a multiple unit system such as a capsule containing extended and immediate release beads.

Extended release tablets containing hydrophilic polymers are prepared by techniques commonly known in the art such as direct compression, wet granulation, or dry granulation. Their formulations usually incorporate polymers, diluents, binders, and lubricants as well as the active pharmaceutical ingredient. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release formulations are created by coating a solid dosage form with a polymer film, which is insoluble in the acidic environment of the stomach, and soluble in the neutral environment of the small intestine.

The delayed release dosage units can be prepared, for example, by coating a drug or a drug-containing composition with a selected coating material. The drug-containing composition can be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and can be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename Eudragit® (Rohm Pharma; Westerstadt, Germany), including Eudragit® L30D-55 and L100-55 (soluble at pH 5.5 and above), Eudragit® L-100 (soluble at pH 6.0 and above), Eudragit® S (soluble at pH 7.0 and above, as a result of a higher degree of esterification), and Eudragits® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials can also be used. Multi-layer coatings using different polymers can also be applied.

The preferred coating weights for particular coating materials can be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition can include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates can also be used. Pigments such as titanium dioxide can also be used. Small quantities of an anti-foaming agent, such as a silicone (e.g., simethicone), can also be added to the coating composition.

Alternatively, each dosage unit in the capsule can comprise a plurality of drug-containing beads, granules or particles. As is known in the art, drug-containing "beads" refer to beads made with drug and one or more excipients or polymers. Drug-containing beads can be produced by applying drug to an inert support, e.g., inert sugar beads coated with drug or by creating a "core" comprising both drug and one or more excipients. As is also known, drug-containing "granules" and "particles" comprise drug particles that may or may not include one or more additional excipients or polymers. In contrast to drug-containing beads, granules and particles do not contain an inert support. Granules generally comprise drug particles and require further processing. Generally, particles are smaller than granules, and are not further processed. Although beads, granules and particles can be formulated to provide immediate release, beads and granules are generally employed to provide delayed release.

EXAMPLES

PBZ Mutant CHFR Fails to Induce Taxane Resistance in CHFR Deficient NSCLC Cell Lines Transfection of wt-CHFR into CHFR deficient cells has been shown to restore the antephase checkpoint leading to a pre-mitotic cell cycle arrest after taxane challenge and ultimately to confer de-novo resistance to taxanes. In Hela cells, full length, but not PBZ-mutant CHFR has similar cell cycle effects. To determine the functional relevance of the PBZ domain on taxane resistance in NSCLC CHFR deficient CALU-6 cells were transfected with either with full-length CHFR (pDEST40-wt-CHFR) or PBZ mutant CHFR (pDEST40-CHFR-PBZ*). Cell viability assays showed that only transfection of wt-CHFR confers resistance to taxanes when compared to both transfection of empty vector or the PBZ mutant variant (FIG. 1A). These findings highlight the importance of an intact PBZ domain for an intact checkpoint function and CHFR mediated taxane resistance, since the CHFR-PBZ* construct did not affect taxane sensitivity compared to empty vector.

The CHFR PBZ Domain Mediates Interactions with Parylated PARP1

Figure 1B:
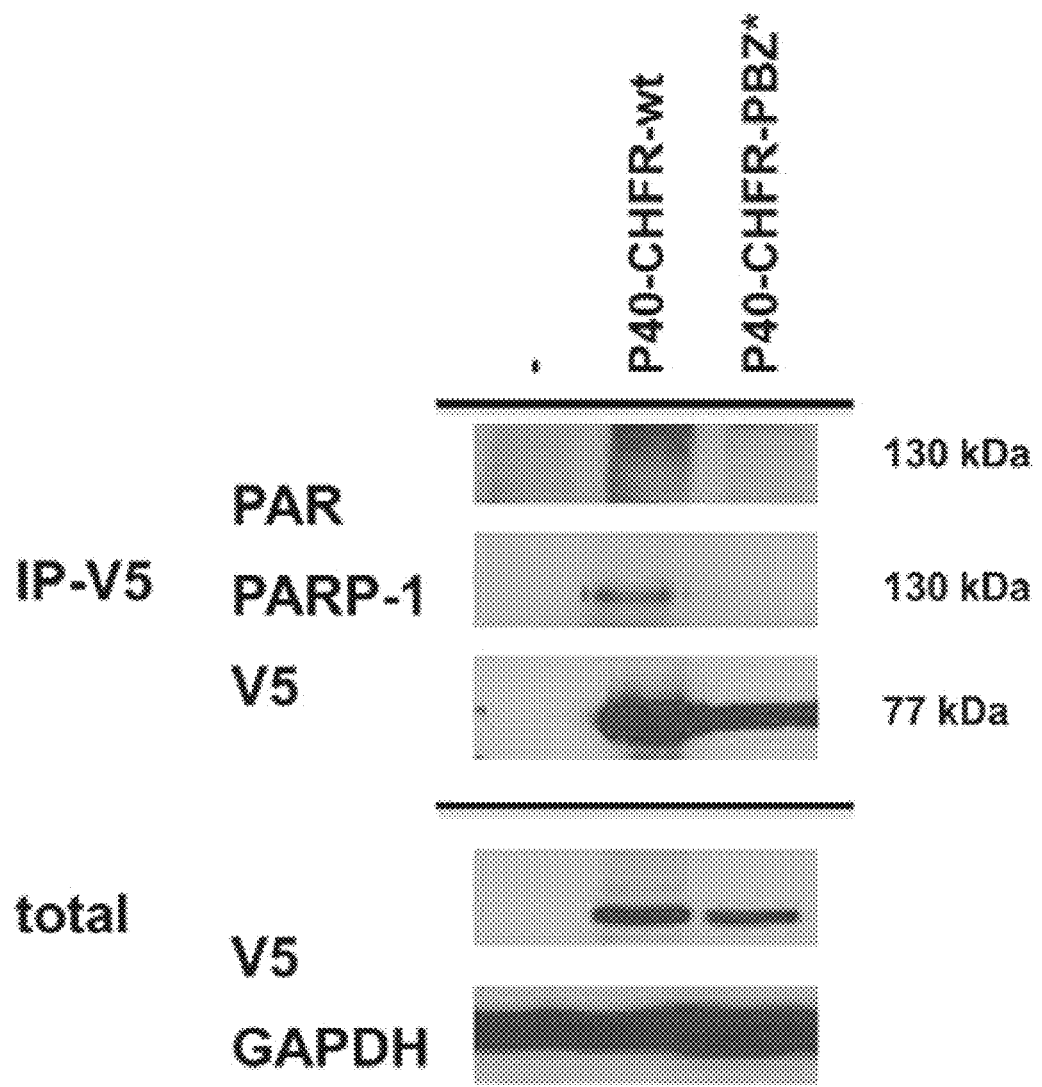
FIG. 1B shows data where pDEST40-wt-CHFR and p40-CHFR-PBZ* was transfected into HEK293 cells. After immunoprecipitation with an anti-V5 antibody, an interaction only between wt-CHFR and PAR and PARP1 was demonstrated.
Figure 1C:
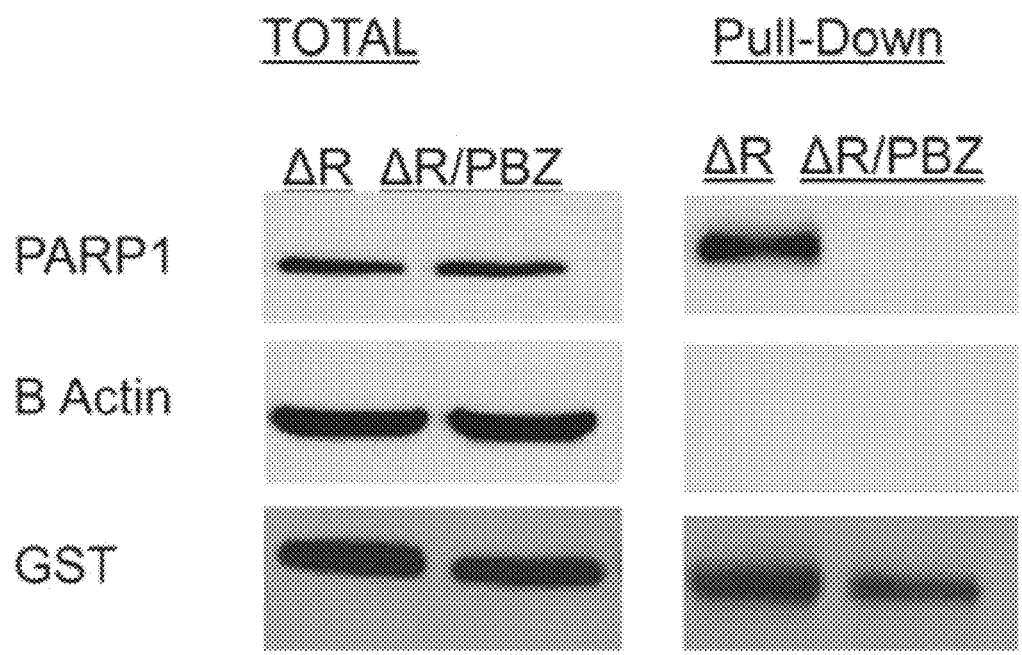
FIG. 1C shows data where pDEST27-ΔR-CHFR and pDEST27-ΔR-CHFR-PBZ* were stably transfected into HEK293 cells. Deletion of the RING domain stabilized and equalized protein levels of both constructs. After affinity purification with a gluthathione resin, only the CHFR mutant with an intact PBZ domain (-ΔR-CHFR) interacted with PARP1. Mutation in the PBZ domain (-ΔR-CHFR-PBZ*) completely abrogated this interaction.
Figure 1D:
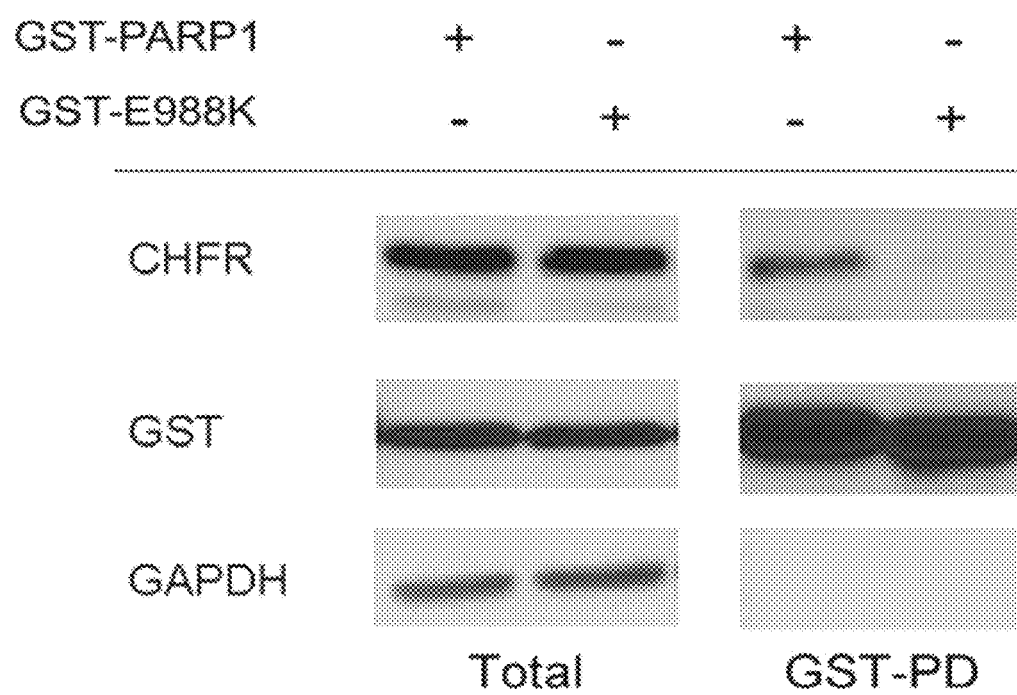
FIG. 1D shows data where pDEST27-PARP1 and enzymatically deficient pDEST27-PARP1-E988K were transfected into HEK293 cells. After glutathione-affinity purification, an interaction with CHFR was only demonstrated for the catalytically intact wt-PARP1, suggesting that autoparylation of PARP1 is required for the interaction with CHFR.

To determine possible interactions between CHFR and other proteins that depend on an intact PBZ domain, the empty pDEST40 vector, pDEST40-wt-CHFR or pDEST40-CHFR-PBZ* vectors were transfected into HEK293 cells and immunoprecipitation for V5-tagged CHFR was performed. Western blot analysis for poly ADP ribosylated (PAR) proteins revealed one prominent band at ~130 kDA interacting only with wt-CHFR but not CHFR-PBZ*, suggesting an interaction with one major species of PARylated protein. Given that the molecular weight of parylated PARP1 is approximately 130 kDA, we performed a western blot for PARP1, which confirmed an interaction between CHFR and PARP1 (FIG. 1B). Since protein expression of a PBZ mutant CHFR construct is unstable, either wt-CHFR or CHFR-PBZ constructs were transfected with an additional deletion of the RING domain. These constructs show preserved and equal protein expression. Mutation of the CHFR-PBZ domain abolished the interaction between CHFR and PARP1, indicating that the interaction requires an intact PBZ domain (FIG. 1C). The reciprocal interaction between PARP-1 and CHFR was also detected in HEK 293 cells expressing GST tagged wt-PARP-1 (FIG. 1D). To determine if the interaction between CHFR and PARP1 is parylation dependent or independent, a catalytically dead mutant of PARP1 (E988K) was generated which completely lacks the ability to synthesize PAR. Only wt-PARP1 showed an interaction with CHFR (FIG. 1D), suggesting that the interaction between these two proteins is parylation-dependent. Taken together, these data indicate that CHFR preferentially interacts with the parylated form of PARP-1, and that this interaction is mediated by the CHFR PBZ domain.

The Interaction with PARP1 Stabilizes CHFR Protein

Figure 1E:
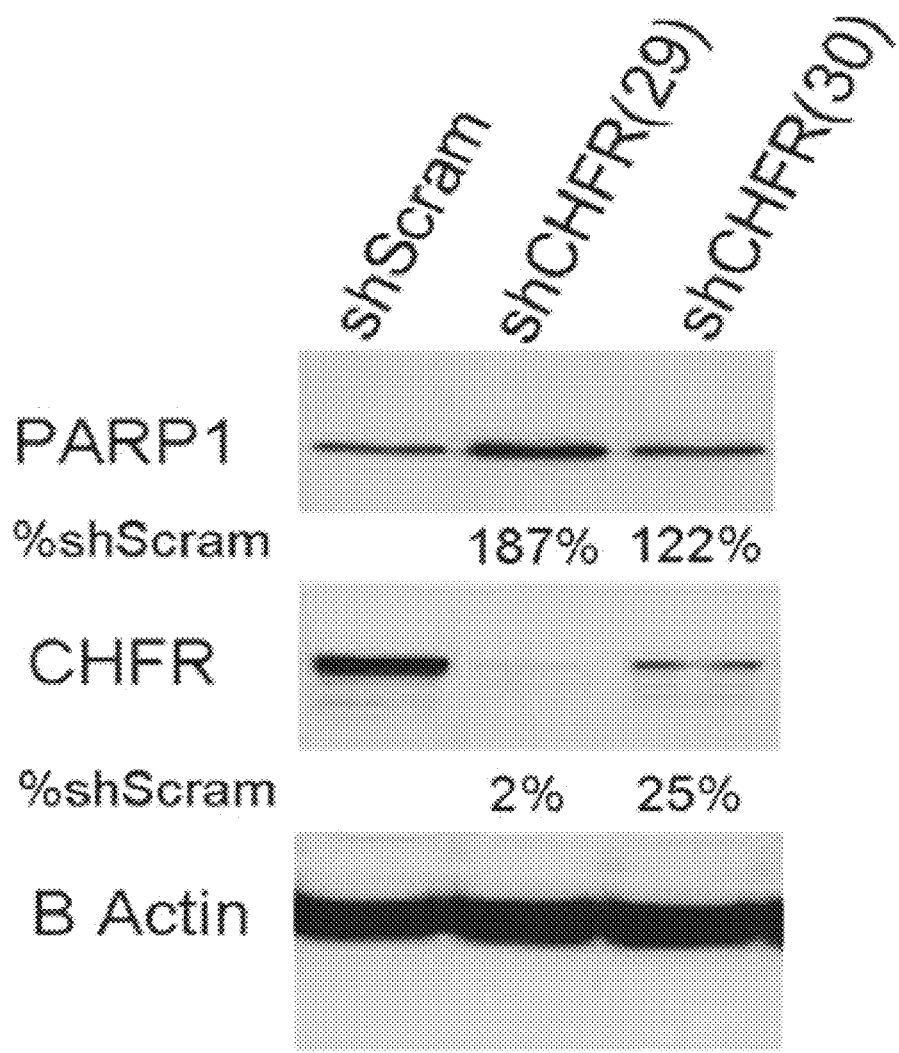
FIG. 1E shows data indicating a stable shRNA knockdown of CHFR in A549 cells leads to a reduction in PARP1 protein levels compared to scrambled shRNA; (number indicates stable cell line annotation).
Figure 1F:
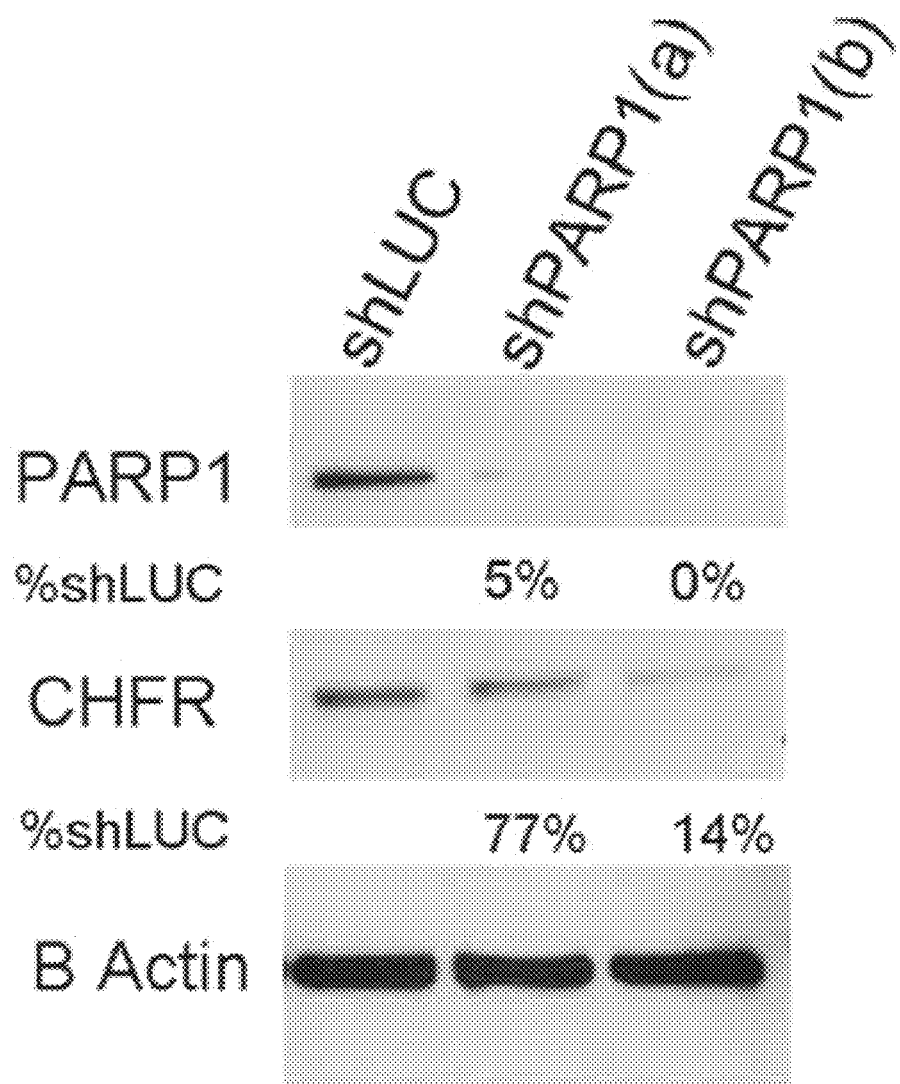
FIG. 1F shows data indicating stable shRNA knockdown of PARP1 in A549 cells leads to a reduction in CHFR protein levels compared to luciferase targeted shRNA (number indicates stable cell line annotation).
Figure 1G:
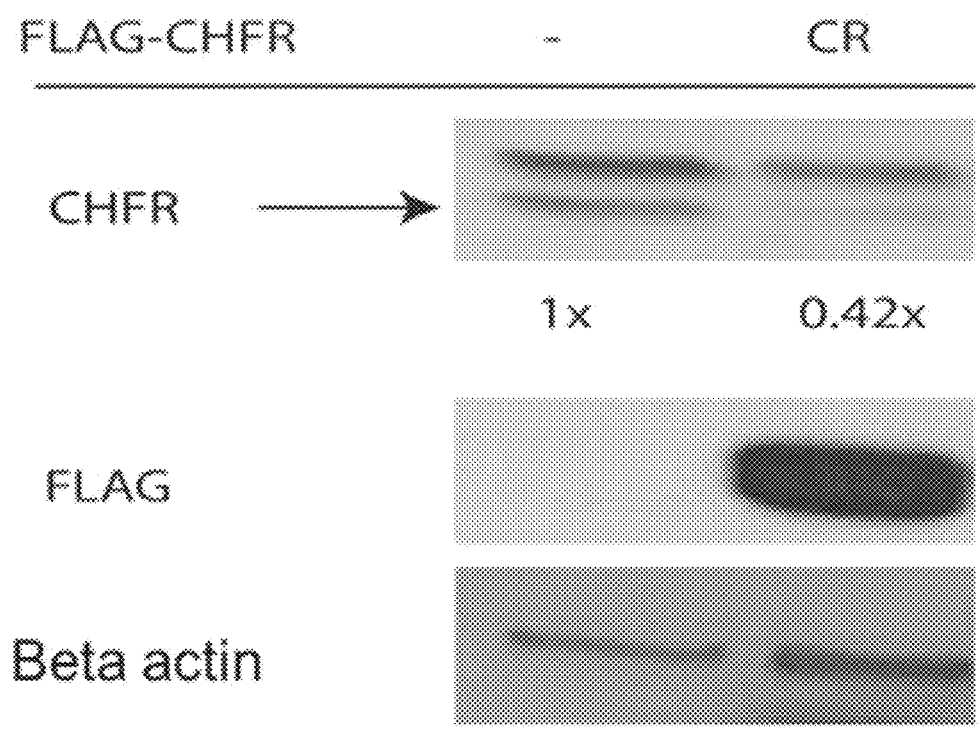
FIG. 1G shows data indicating Native CHFR protein levels in A549 cells are reduced by overexpression of a FLAG tagged PBZ-domain peptide as competitor for parylated-PARP1.

The impact of CHFR on PARP1 stability was evaluated. shRNAs were used to generate stable knockdowns in HEK293 cells. CHFR knockdown led to an increase in PARP-1 protein expression (FIG. 1E). This phenomenon has previously been attributed to the decrease in proteasomal degradation of PARP1. Conversely and interestingly, PARP1 knockdown led to a significant reduction in CHFR protein expression (FIG. 1F). These findings suggest that the interaction with PARP1 stabilizes the CHFR protein, possibly by protecting it from degradation. If the interaction with PARP1 protects CHFR from degradation, then CHFR protein levels should be reduced by competing for this interaction. To test this hypothesis, a Flag-tagged PBZ domain was overexpressed alone in HEK293 cells. Indeed, CHFR protein levels were reduced in cells expressing the PBZ domain as compared to those transfected with empty vector (FIG. 1G). Together, these results demonstrate that CHFR protein is indeed stabilized by its interaction with PARP1 which is mediated by CHFR's PBZ domain.

CHFR Degradation in PBZ Mutant CHFR is Mediated by Autoubiquitination

Figure 1H:
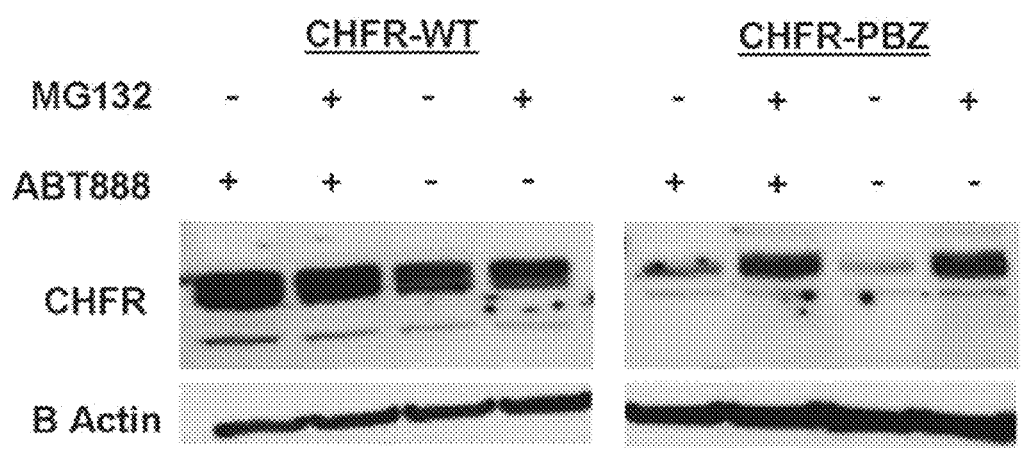
FIG. 1H shows data indicating stable transfection of CHFR-PBZ* in Calu-6 cells leads to only low levels of expression, proteasomal inhibition with MG-132 increases CHFR-PBZ* protein levels. Treatment with the PARP-inhibitor ABT-888 does not have a significant impact on either wt-CHFR or CHFR-PBZ* levels.
Figure 11:
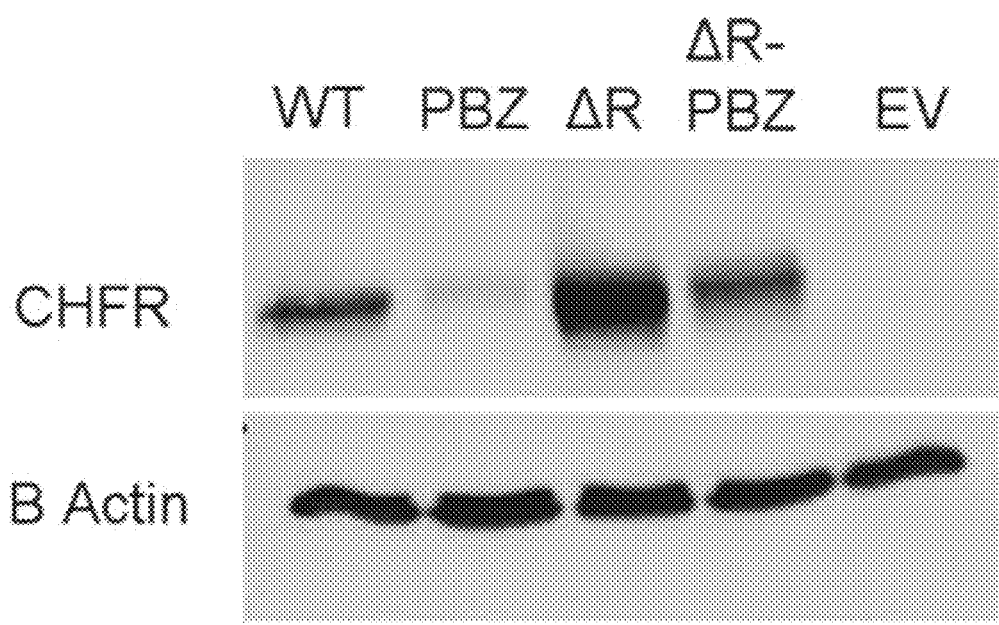

Regulation of CHFR protein levels has been shown to be at least in part dependent on autoubiquitination mediated by its RING domain. To determine if disruption of the CHFR-PARP1 interaction forces CHFR degradation by auto-ubiquitination and subsequent proteasomal degradation, wild-type and the CHFR-PBZ mutant were expressed in the presence and absence of the proteasome inhibitor MG-132 (FIG. 1H) or after the additional deletion of the RING domain (FIG. 1I) in Calu-6 cells. While the CHFR PBZ mutant protein is only expressed at very low levels, both inhibition of the proteasome or deletion of the RING domain restored PBZ mutated CHFR expression to levels that were comparable to those of the wt-CHFR. These data are consistent with the interpretation that disruption of the CHFR-PARP interaction results in auto-ubiquitination and degradation of CHFR. Pharmacologic inhibition of PARP1's polymerase activity by the PARP-inhibitor ABT-888 did not result in altered CHFR protein levels (FIG. 1H).

Figure 2A:
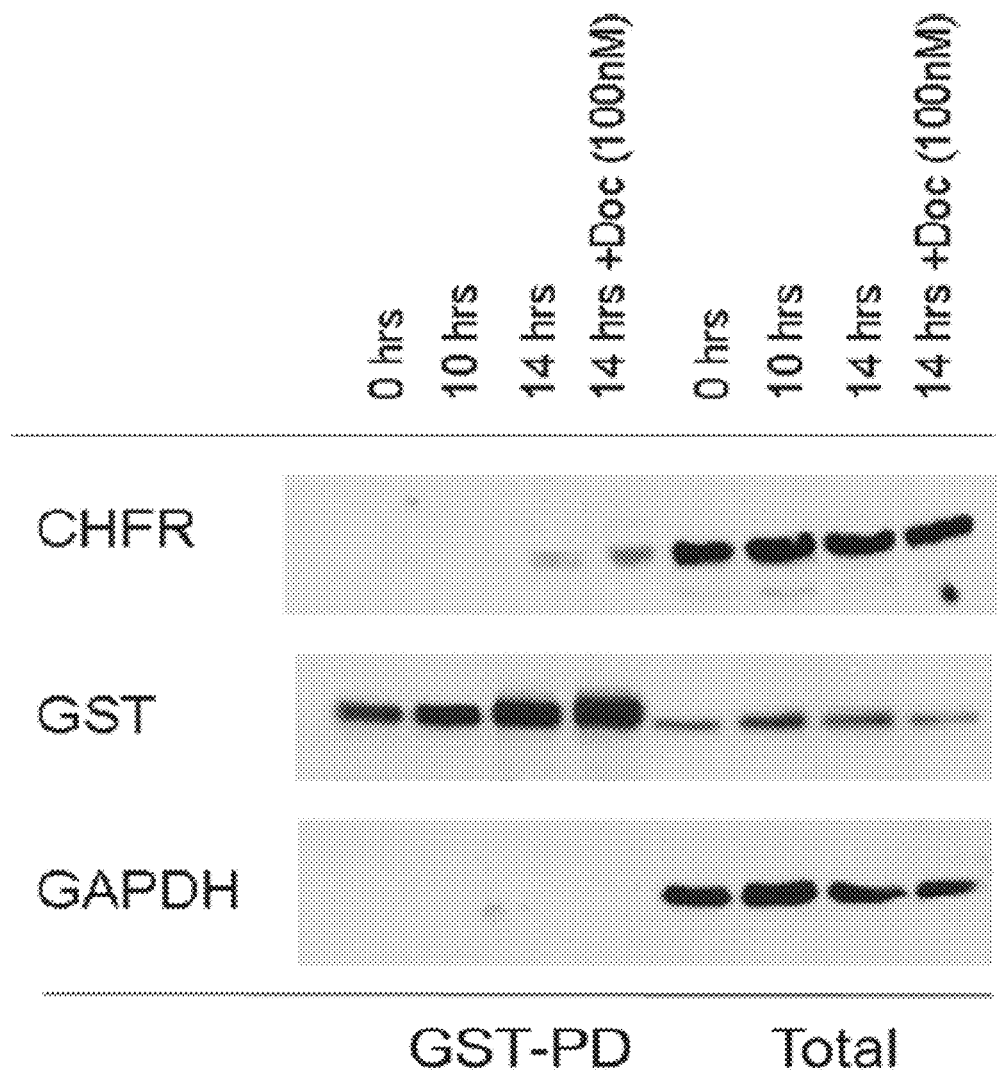
FIG. 2A shows data in aphidocholin synchronized A549 cells indicating an interaction between GST-tagged PARP1 and CHFR is predominantly observed in the G2/M phase of the cell cycle.
Figure 2B:
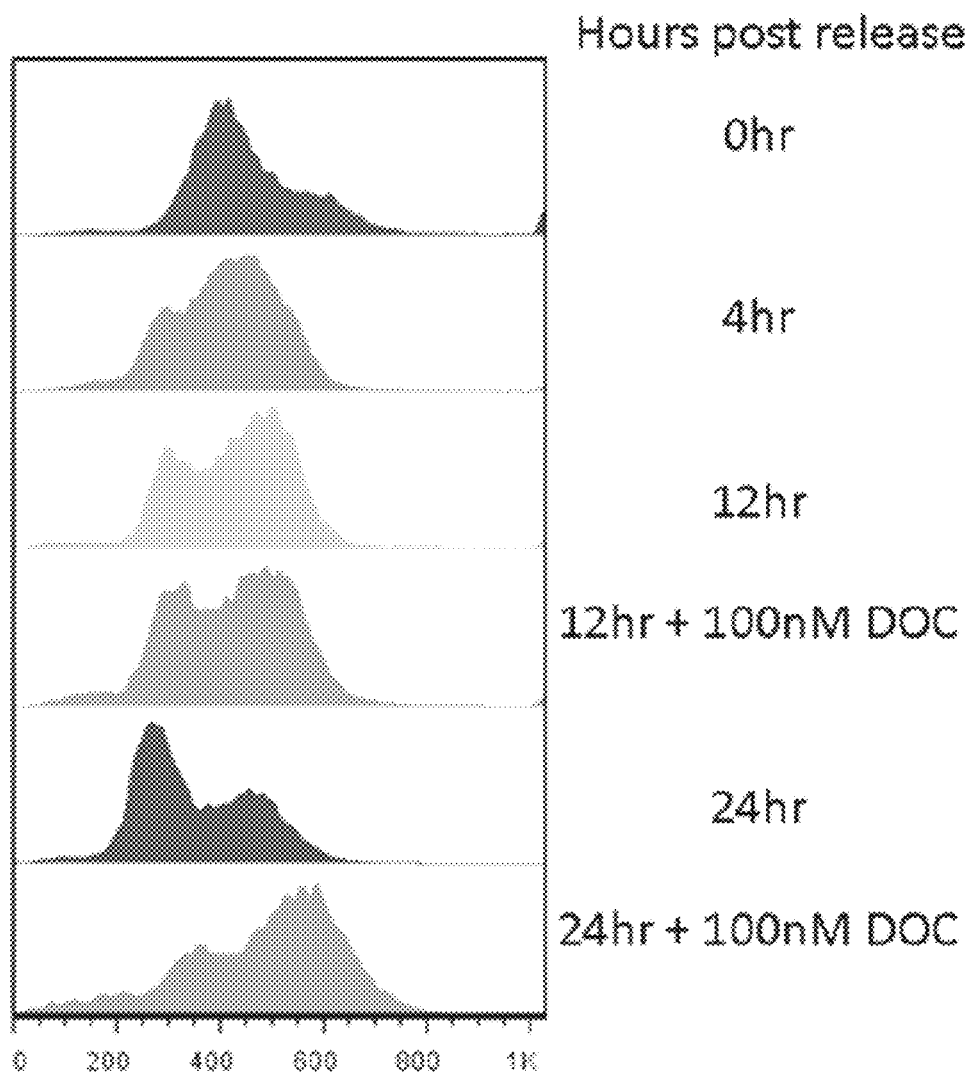
FIG. 2B shows data indicating induction of microtubular damage with docetaxel further enhances this interaction, suggesting a central role in mediating the antephase checkpoint.
Figure 2C:
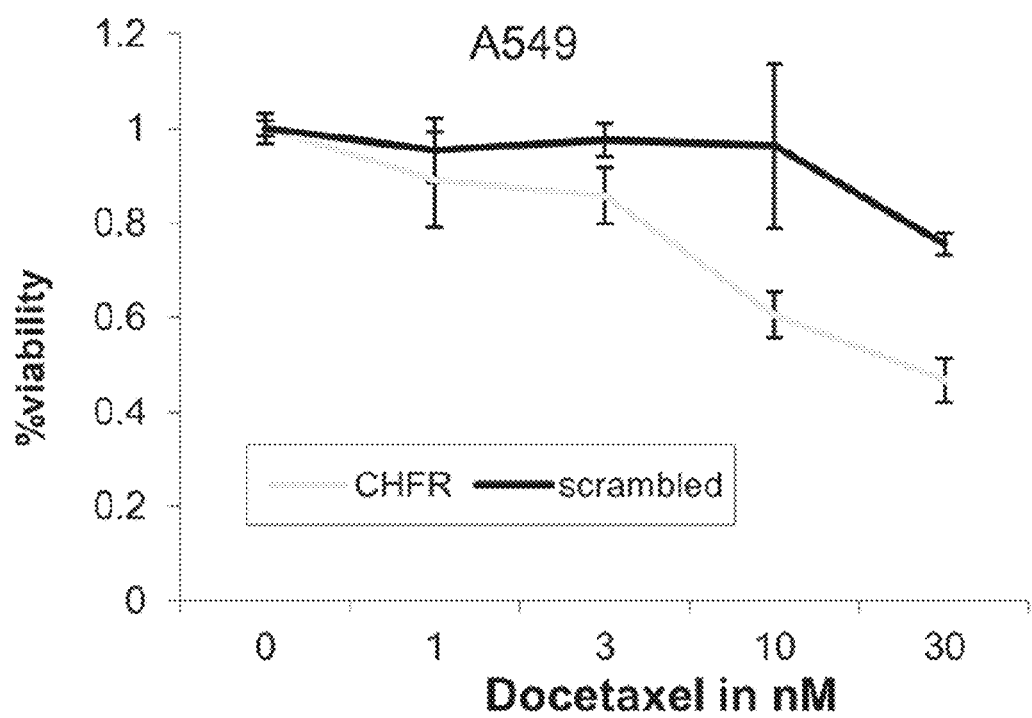
FIG. 2C shows data from a knockdown of CHFR.
Figure 2D:
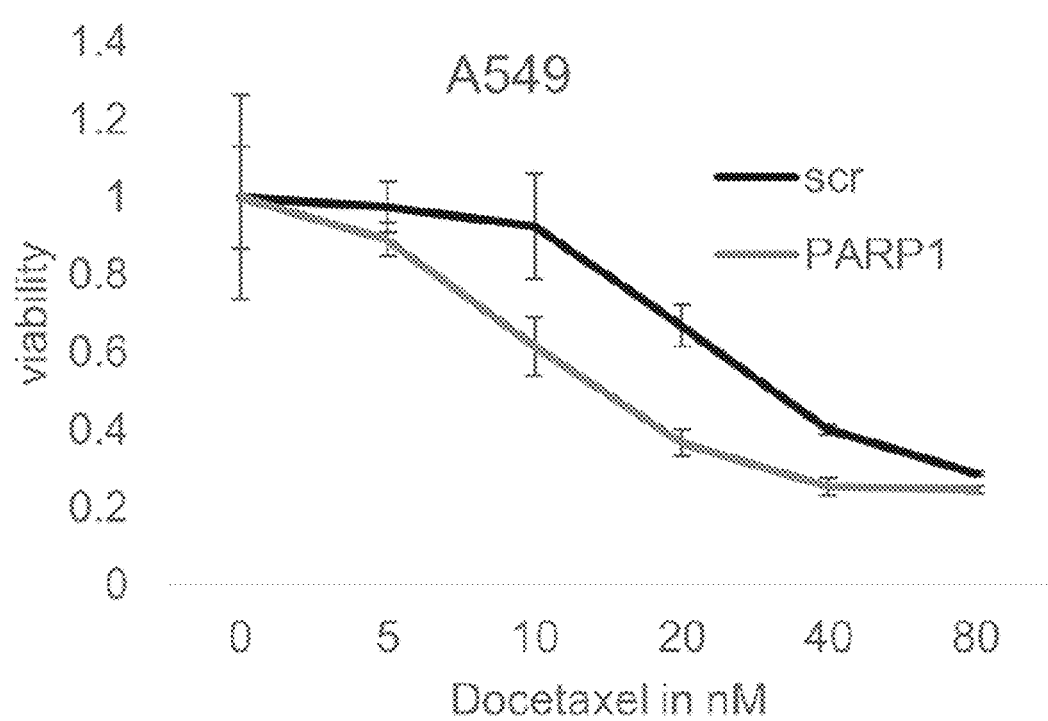
FIG. 2D show data from a knockdown indicating PARP1 sensitizes stably transfected A549 cells to docetaxel compared to scrambled control shRNA.

The CHFR-PARP1 Interaction is Cell Cycle Dependent and Enhanced by Docataxel Induced Mitotic Stress The functional significance of the interaction between CHFR and PARP1 in antephase checkpoint control and taxane sensitivity was evaluated. HEK293 cells were transfected with a GST-tagged PARP1, synchronized with aphidocholin, and the interaction between GST-tagged PARP1 and CHFR was analyzed at various stages of the cell cycle (FIG. 2A, 2B). The interaction between PARP1 and CHFR was limited to the G2/M phase of the cell cycle and was further enhanced by additional exposure to mitotic stress, suggesting a specific role of this interaction in the control of mitotic entry. To determine the effect on taxane sensitivity, XTT assays were performed in A549 cells stably transfected with either shRNAs specifically targeting CHFR or PARP1 or control shRNAs (scrambled or luciferase targeting respectively). CHFR-deficient A549 cells showed an increased sensitivity to docetaxel relative to A549 cells expressing a scrambled control (FIG. 2C). Interestingly, PARP1 deficient cells also showed increased sensitivity to docetaxel (FIG. 2D), likely due to the reduction in CHFR expression that accompanies PARP1 knockdown (FIG. 1G). These findings show that not only CHFR is required for a functional mitotic checkpoint, but that additionally PARP1 is also an important mediator of taxane resistance.

PARP-Inhibition Fails to Induce Synergistic Cytotoxicity in CHFR Expressing Lung Cancer Cell Lines Hypothesizing that PARP-inhibition could induce synergistic cytotoxicity in CHFR expressing lung cancer cell lines, cytotoxicity assays were performed in seven lung cancer cell lines (A549, EKVX, H596, H522, Hop-62, H460 and H2023) using docetaxel and the PARP-inhibitor ABT-888 either alone or in combination. Synergy was not observed in any of the cell lines. Also, combination of docetaxel with a dose of ABT-888 (20 uM), which achieves PARP inhibition in vitro, did not lead to enhanced cytostasis. In vitro, ABT-888 did not reduce CHFR protein expression (FIG. 1H) nor did it disrupt the interaction between CHFR and PARP-1, suggesting that PARP-1 inhibition is insufficient to force CHFR into auto-degradation. Whether a pharmacologic strategy that mimics the effects of a PBZ domain mutation and completely inhibits the binding of parylated proteins in the PBZ domain may be superior to PARP-1 inhibition in the sensitization against taxanes was evaluated.

Figure 3A:
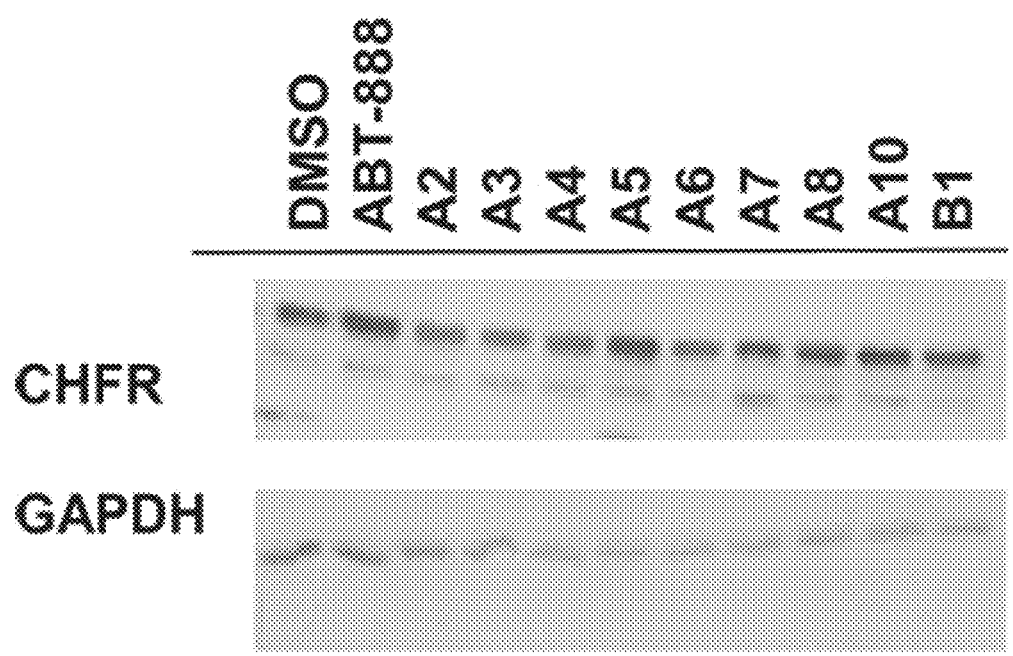
FIG. 3A shows data from a high-throughput computational screen of 5,256,508 chemical structures against the published crystal structure of CHFR's PBZ domain was performed. The 10 compounds with the highest docking scores were tested for their ability to regulate CHFR expression levels. Several compounds, termed 'A2', 'A3', 'A4' and 'A6' reduced CHFR expression after 24 hours at 10 uM in A549 cells.
Figure 3B:
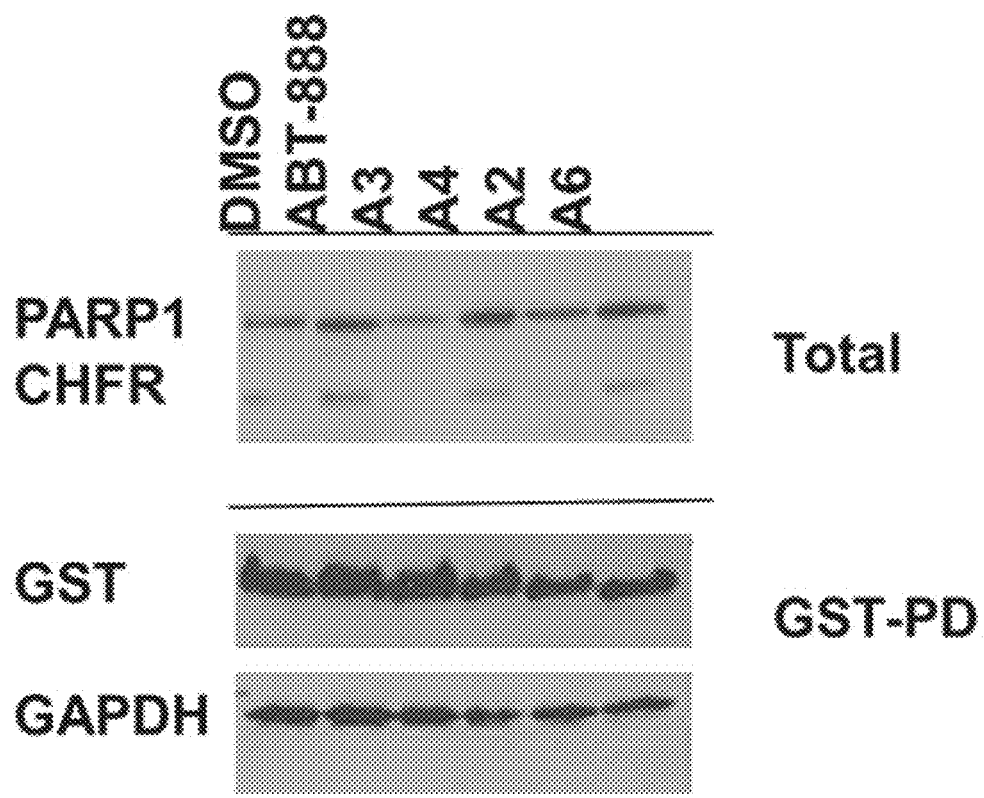
FIG. 3B shows data on Hek293 cells with stable expression of pDEST27-PARP1, were treated with either DMSO or 'A3' at 10 uM, or ABT-888 10 uM for 16 hours and subjected to gluthathione affinity purification for GST tagged PARP1. Only A3 completely inhibited an interaction between PARP1 and CHFR.
Figure 3C:
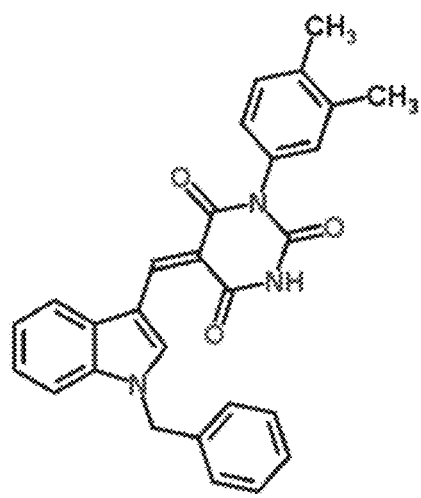
FIG. 3C shows the Chemical structure of A3.
Figure 3D:
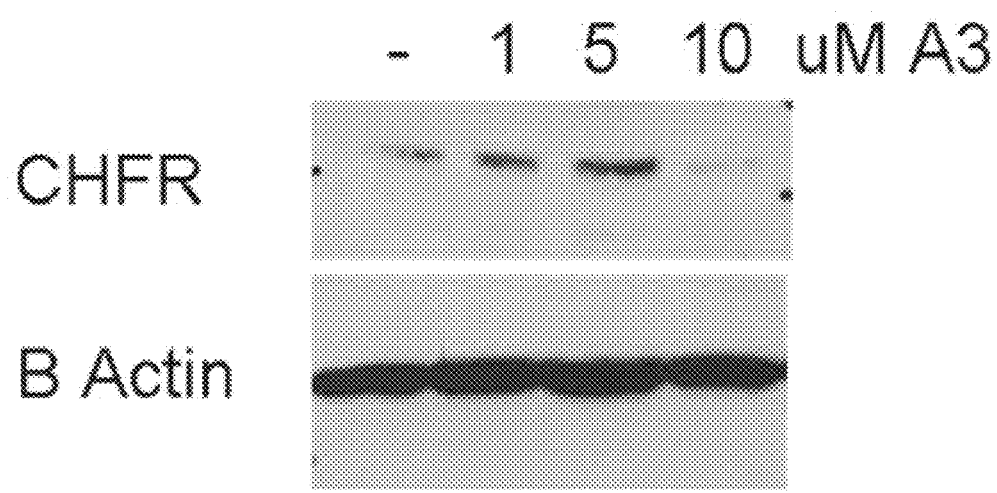
FIG. 3D shows data on A549 nuclear extracts treated with vehicle (dmso) or indicated A3 concentration for 16 hrs, CHFR is lost from the nuclear extract at 10 uM A3. HEK293 cells were stably transfected with the pDEST27-AR-CHFR construct. Deletion of the RING domain in this construct leads to both stable CHFR and PARP1 expression that is unaltered by treatment with increasing concentrations of 'A3' for 16 hours. Nonetheless, the interaction between glutathione-affinity purified CHFR-ΔR and PARP1 was decreased by 'A3' in a dose dependent fashion. A549 cells were incubated for 16.5 hrs with MG132 and indicated A3 concentration for 16 hrs. At 10 uM A3 concentration CHFR staining is diminished in the nucleus Cells are stained with CHFR. Co-exposure of unsynchronized cells to docetaxel and 'A3' for 24 hours prevents the docetaxel induced cell cycle arrest, suggesting functional disruption of the antephase checkpoint.

High-Throughput Computational Screening Identifies a Small Molecule Inhibitor of the CHFR/PARP1 Interaction In an attempt to generate possible lead compounds for the pharmacologic inhibition of the CHFR-PARP1 interaction, a high throughput computational screen of 5,256,508 chemical structures in the MCULE database of purchasable compounds using the AutoDockVina algorithm against the published crystal structure of the CHFR-PBZ domain was performed. The 10 most promising 'hits' based on Autodock Vina docking scores (<−9.7) were selected for further characterization. Commercially available compounds were tested for their impact on nuclear CHFR levels (FIG. 3A). Several compounds, including 'A2', 'A3', 'A4' and 'A6' decreased CHFR levels assayed by western blotting of whole cell extracts. The impact of the above referenced compounds on the PARP1/CHFR interaction were evaluated. HEK293 cells were transfected with GST tagged PARP1 and the interaction with CHFR determined in pull down assays for those 4 compounds. Only 'A3' completely prevented the PARP1-CHFR interaction at 10 uM concentration (FIG. 3B). In contrast to treatment with ABT-888, 'A3' completely disrupted the interaction between GST-tagged PARP-1 and CHFR (FIG. 3B). Importantly, In vitro parylation studies showed that 'A3' has no impact on PARP1 auto-parylation, indicating that the disruption of the PARP1/CHFR interaction by 'A3' is not dependent on de-parylation of PARP1, but rather the interaction between CHFR and parylated PARP1. Since it is possible that the co-immunoprecipitation between PARP-1 and CHFR after 'A3' treatment was negative due to the fact that CHFR was degraded, the experiment was repeated after transfection with the Ring-domain deleted ΔR-CHFR construct, which maintained both stable CHFR and PARP1 levels even after treatment with 'A3'. However, 'A3' treatment resulted in a dose dependent inhibition of the interaction between CHFR and PARP1, suggesting a specific inhibitory effect of 'A3' on this protein interaction. These observations were confirmed by data that show a dose dependent regulation of CHFR protein levels by 'A3' (FIG. 3D). Interestingly, however, at low concentrations of 'A3' an initial increase in CHFR protein levels was observed, followed by complete disappearance of CHFR at the 10 uM concentration. Since CHFR's mitotic checkpoint function is predominantly executed in the nucleus, the effects of 'A3' treatment on nuclear localization of CHFR were evaluated. 'A3' in combination with MG-132 lead to a depletion of nuclear CHFR and accumulation of cytoplasmic CHFR, suggesting the possibility that 'A3' may indeed be capable of disrupting the antephase checkpoint.

Cell cycle arrest at G2/M in response to microtubular damage is a hallmark of a functional antephase checkpoint. To test the functional relevance of our newly discovered CHFR small molecule inhibitor 'A3', unsynchronized A549 cells were exposed for 12 hours to docetaxel (50 nM) with or without 'A3' (10 uM) and the cell cycle stages were analyzed by flow-cytometry. 'A3' exposure prevented docetaxel induced cell cycle arrest, suggesting that 'A3' functionally disrupted the antephase checkpoint.

Figure 4A:
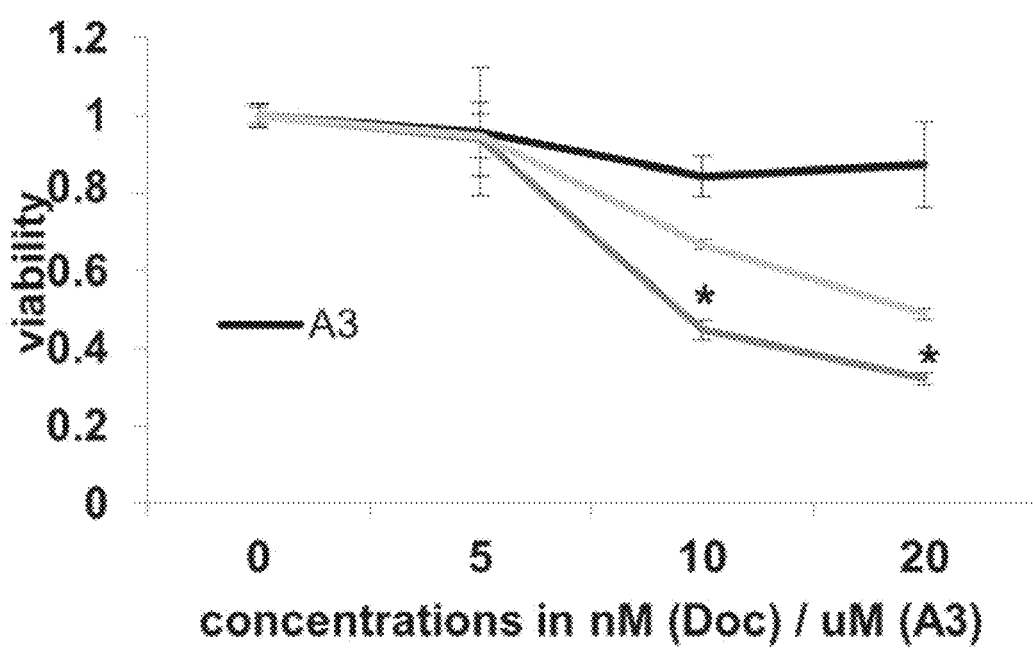
FIG. 4A shows data from cell viability experiments performed after exposure to 'A3' (5-20 uM), docetaxel (5-20 nM) or the combination of both compounds for 72 hours. At the 10 and 20 nM concentrations, there was statistically significantly decreased viability in the combination treated cells. (*=$p<0.01$).
Figure 4B:
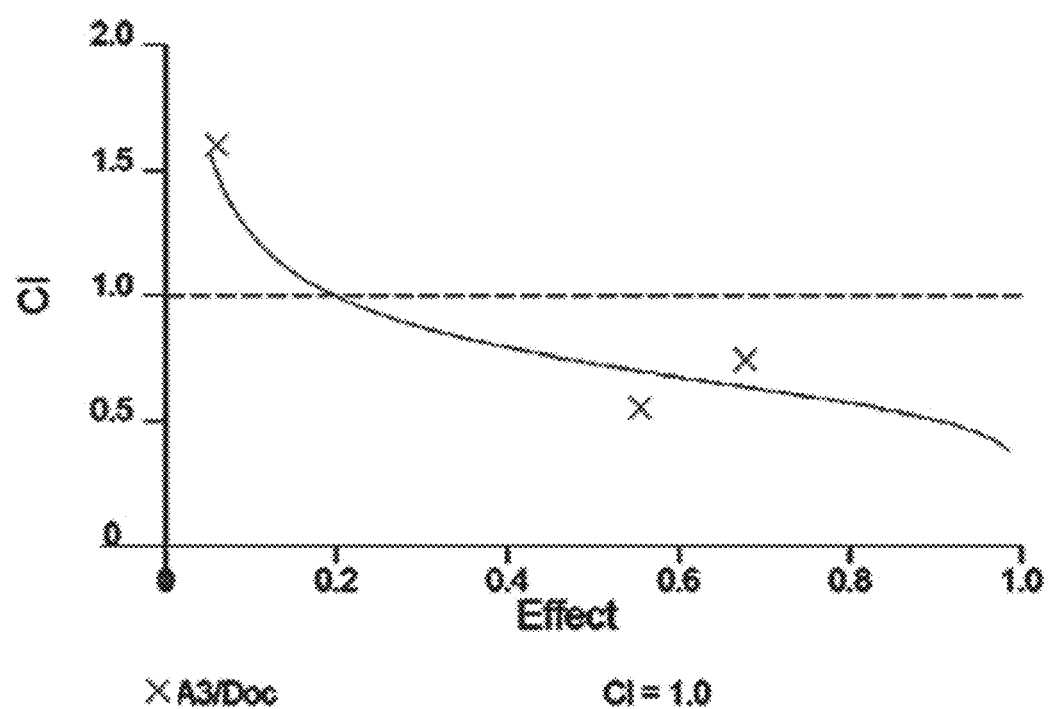
FIG. 4B shows the combination index calculated according to the method of Chou-Talaley. 'A3' and docetaxel exert synergistic effects at the 10 and 20 uM/nM concentrations stable shRNA knockdown of PARP1 or CHFR reverses synergy between A3 and docetaxel in A549 cells in colony formation assays compared with scramble shRNA control (*=$p<0.05$).
Figure 4C:
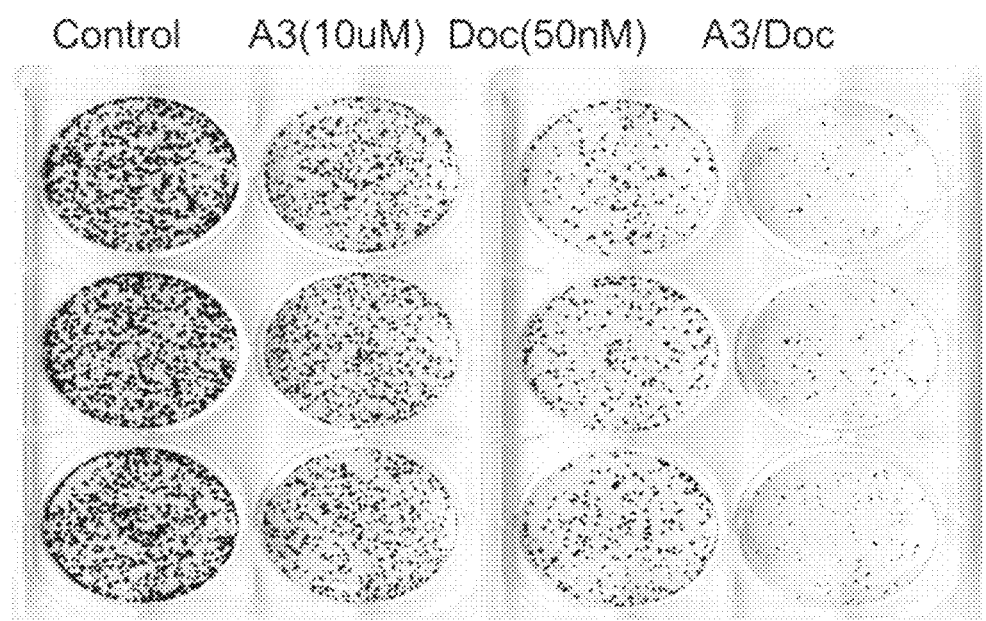
FIG. 4C shows data on the interaction between docetaxel and 'A3' in colony formation assays. Various cell lines of different tissues of origin and with different CHFR expression status were exposed to 1 hour of docetaxel and 72 hours of 'A3'. Effects were defined as 1−colony count (treatment)/colony count (control). The nature of the interaction between the two compounds was analyzed by the Bliss additivity method. A representative example of the colony formation assays is shown in the CHFR expressing cell line H460 where strong synergy between 'A3' and docetaxel is observed. For subsequent colony formation assays, cell lines were characterized into CHFR expressing vs. CHFR deficient cell lines by Western-Blot.
Figure 4D:
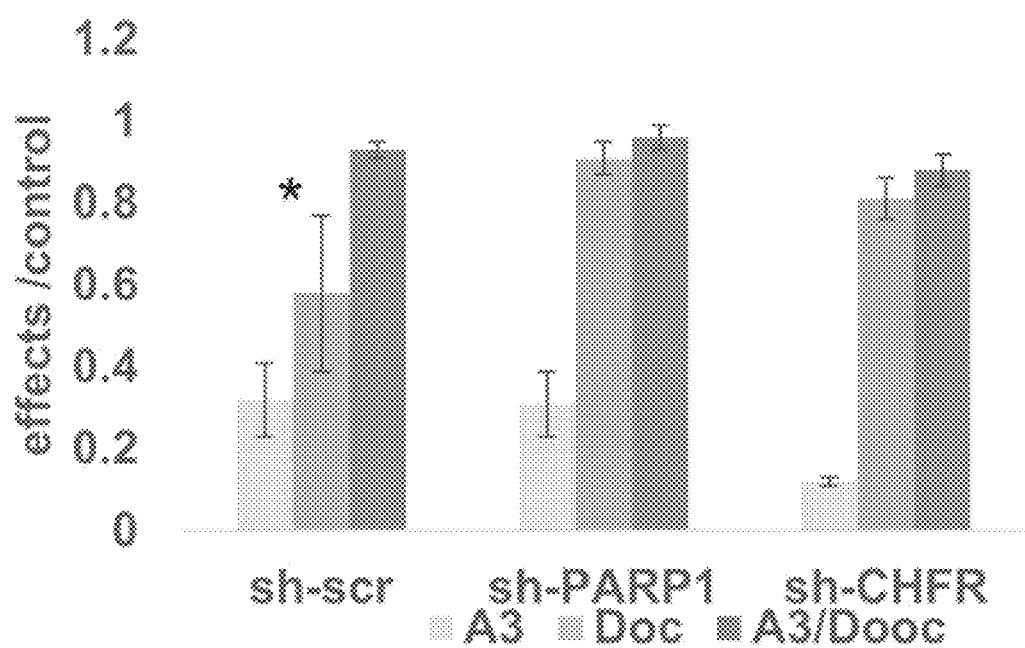
FIG. 4D knock-down of either CHFR or PARP1 in A549 cells alleviates the synergy that is observed in A549 cells transfected with scrambled shRNA. (*=synergy)
Figure 4E:
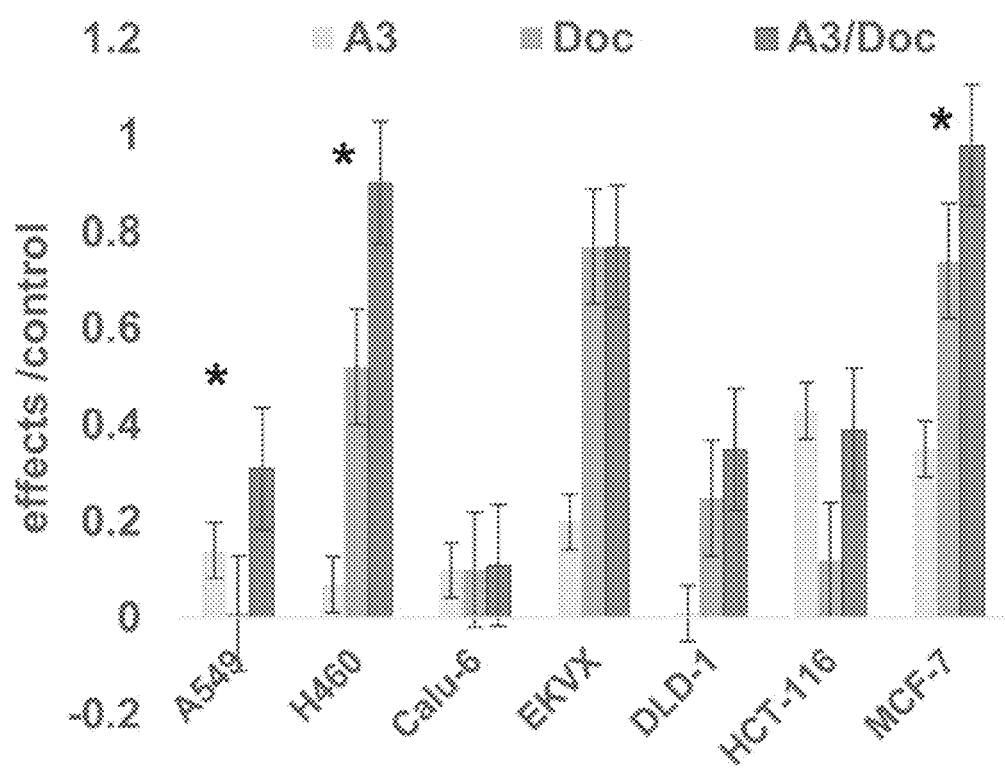
FIG. 4E shows data indicating synergistic effects of A3 and docetaxel in colony formation assays are mostly observed in CHFR expressing cell lines regardless of tumor type. (*=synergy).

Exposure to 'A3' has Synergistic Growth Inhibitory Activity that Correlates with CHFR Expression Similarly to the previous experiments in which CHFR knockdown increased taxane sensitivity in A549 cells, 'A3' and docetaxel showed synergistic growth inhibitory functions in cell viability assays as demonstrated by a Combination index (CI)<1 (FIGS. 4A and 4B). To determine if the synergistic effects of A3 are indeed dependent on an interaction between CHFR and PARP1, colony formation assays were performed in A549 cells transfected with shRNA which was either scrambled or directed against CHFR or PARP1. Synergy between A3 and docetaxel was maintained only in the A549 scramble cell line, but not after CHFR or PARP1 knockdown, suggesting that 'A3's effects are mainly through its on-target effects on the CHFR-PARP1 interaction (FIG. 4D). Finally, colony formation assays were performed on a panel of cell lines of different cancer types such as lung-, breast-, and colon cancer. With the exemption of the EKVX NSCLC cell lines, synergy between 'A3' and docetaxel was observed for all other CHFR expressing cell lines regardless of tumor type supporting the possibility that CHFR targeted therapy may have a wide range of possible applications in those cancer types in which taxanes are frequently used (FIGS. 4C and 4E).

In Vivo Characterization of A3 Levels and Activity

Figure 5A:
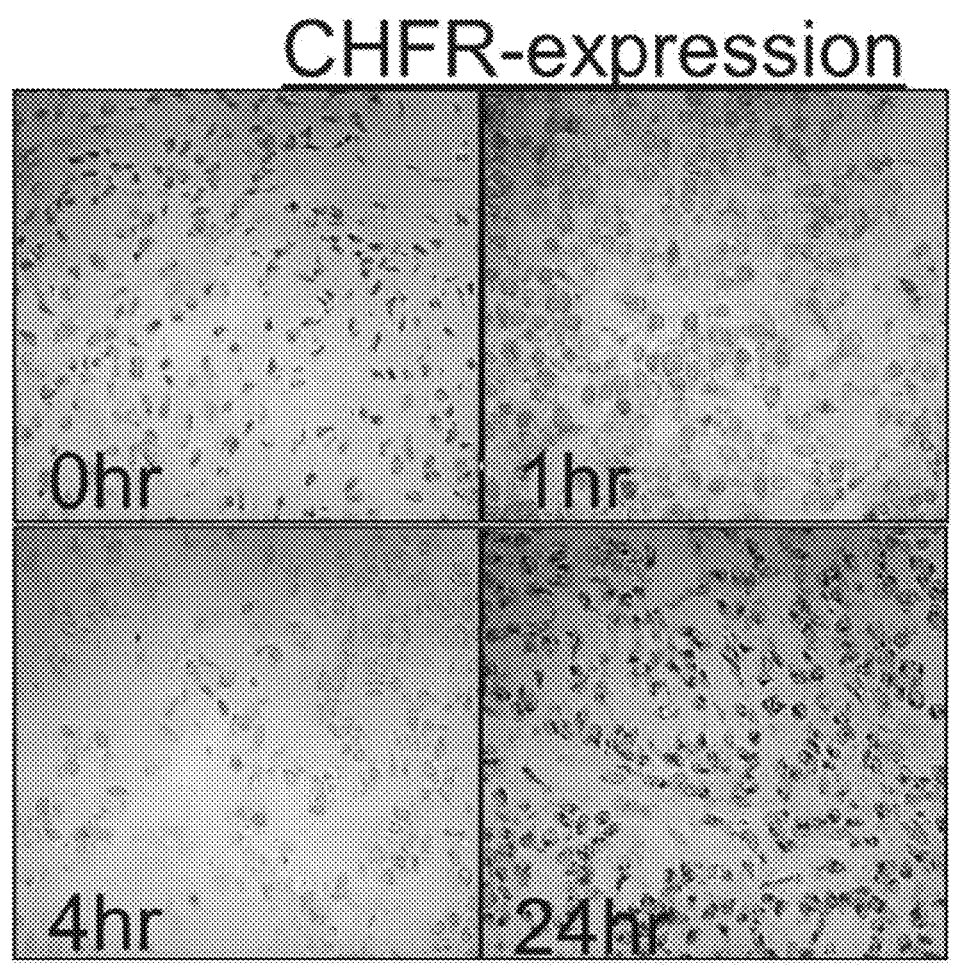
FIG. 5A shows images of 549 cell tumor xenografts in nude mice that were analyzed for CHFR expression at various time points after 'A3' injection. 4 hrs after i.p. injection a significant reduction in nuclear CHFR staining was observed, indicating an in vivo reproducible pharmacodynamic effect of 'A3'.
Figure 5B:
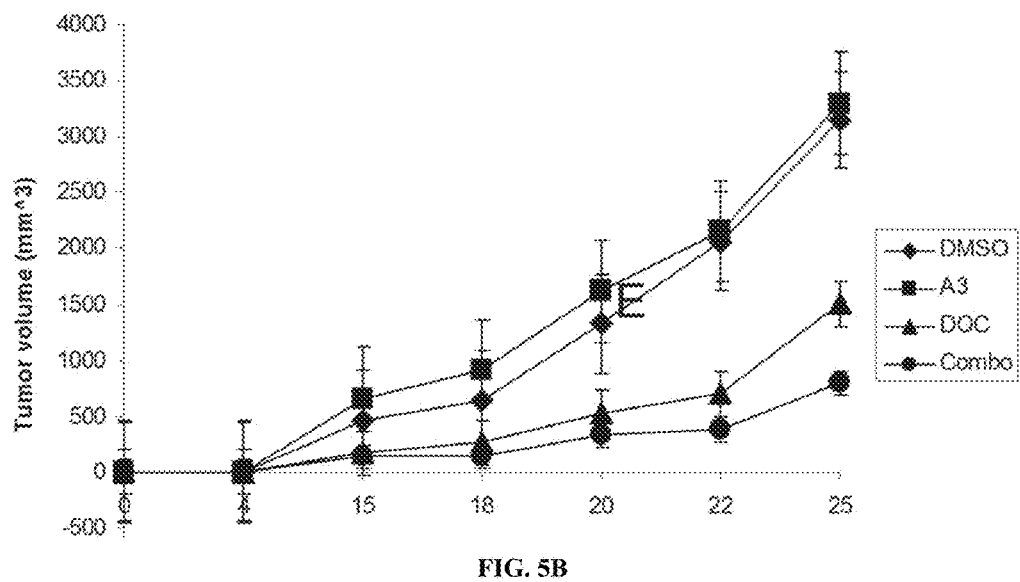
FIG. 5B shows data on tumor size that was measured bi-dimensionally and volumes were calculated by volume=(smallest dimension)2×(largest dimension). While 'A3' treatment alone did not have a discernable anti-tumor effect, combination treatment with 'A3' and docetaxel, proved superior to treatment with docetaxel alone. Pharmacokinetics of A3 were performed at various time points after iv and oral administration of a single dose of 'A3' at 10 mg/kg. $2.5 \times 10^5$ H460 cells were transplanted into the flank of nude mice were. 5 days after transplant, I.P. injection of DMSO, A3, docetaxel, or combination commenced. Explanted tumors are smallest in mice that were treated with combination therapy.

'A3' is capable of disrupting the interaction between CHFR and PARP1 in vitro, leading to a depletion of CHFR expression and to sensitization towards the cytotoxic effects of taxanes. The impact of 'A3' administration on lung tumor xenografts was evaluated. A549 NSCLC cells were injected into the flank of nude mice and allowed to establish for approximately 14 days. Once tumors had reached a volume about 100 mm3, mice received a single ip injection of 'A3' at 10 mg/kg. Mice were then euthanized at 1, 2, 4 and 24 hours after and CHFR in the xenografts was analyzed by immunohistochemistry (FIG. 5A). Significant suppression of nuclear CHFR expression was observed after 4 hours, but was restored to baseline levels at the 24 hr time point.

The in vivo properties of 'A3' were evaluated. The pharmacokinetics of 'A3' after a single oral (25 mg/kg) and intravenous (10 mg/kg) dose of in CD1 mice were determined. Plasma was obtained at pre-specified time points (15 min to 24 hours) and 'A3' concentrations were determined by LC/MS/MS. The data indicated that 'A3' was rapidly and widely distributed following intravenous dosing, and the relative bioavailability of 'A3' from dose normalized AUC values was calculated as 19.5%. Oral bioavailability of 'A3' was insignificant. The time-point of maximal CHFR suppression at 4 hrs follow the peak in A3 plasma levels with some delay.

The in-vivo effects of 'A3', docetaxel and the combination on tumor growth in mouse xenografts, who were previously injected with the H460 cell line were evaluated. Pre-treatment with either DMSO or 'A3' was given 4 hours prior to docetaxel injection, when CHFR expression levels are expected to be the lowest based on the above pharmacodynamic experiments. 'A3' treatment alone did not have a discernable effect on tumor growth when compared to DMSO alone. However, in combination with docetaxel, 'A3' significantly decreased tumor size compared to docetaxel alone, demonstrating that pharmacologic targeting of the CHFR/PARP interaction may indeed be a promising strategy to improve taxane sensitivity in lung cancer.

Combination treatment with 'A3' was not associated with a significant increase in hematologic, hepatic and renal toxicity 10 days after treatment. Representative H&E stained sections of liver and kidneys did not show any toxicity in any of the four treatment arms.

DISCUSSION

Figure 6:
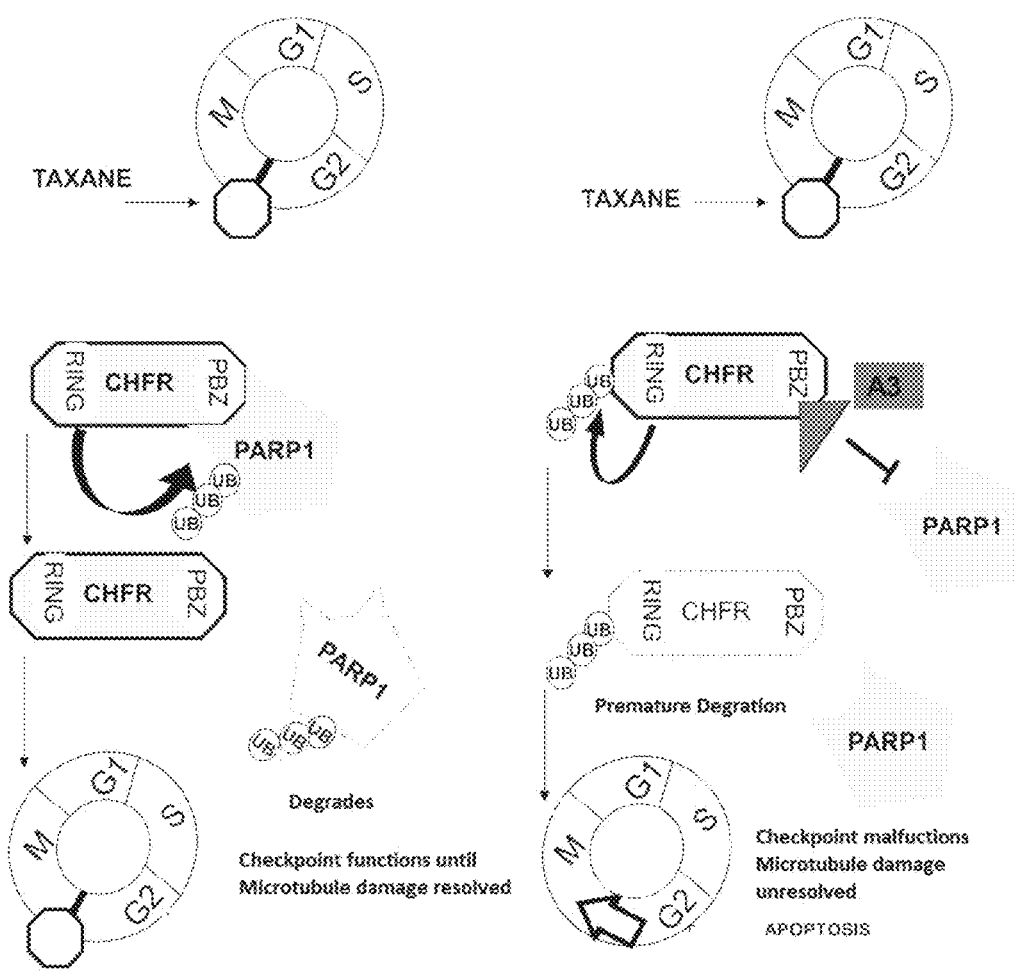
FIG. 6 illustrates a mechanistic model by which the interaction between CHFR and PARP1 may control expression of both proteins. When an interaction is present CHFR targets parylated-PARP1 for proteasomal degradation. PARP1 levels increase with CHFR knockdown. Conversely, a disruption of the interaction between PARP1 and CHFR by the small molecule A3 induces auto-ubiquitination and ultimately destruction of CHFR protein. This in turn leads to disruption of the antephase checkpoint and ultimately mitotic catastrophe in response to taxane challenge.

Although it is not intended that certain embodiments of this disclosure be limited by any particular mechanism, experiments reported herein indicated that the interaction between CHFR and parylated PARP1 stabilizes CHFR protein levels, this interaction is mediated by CHFR's PBZ domain, and that its disruption either by mutation of the PBZ domain or PARP1 knockdown leads to auto-ubiquitination and subsequent proteasomal degradation of CHFR. Reduced CHFR expression in lung cancer is associated with improved survival following platinum taxane based therapy. Taxane sensitivity is increased in gastric-, colon- and cervical cancers in which CHFR is silenced epigenetically. A model is proposed in which pharmacologic inhibition of the CHFR-PARP1 interaction with subsequent loss of CHFR and disruption of antephase checkpoint function helps to overcome intrinsic taxane resistance across a wide spectrum of different tumor types (FIG. 6).

Experiments disclosed herein demonstrate the feasibility of inhibiting the mitotic checkpoint by targeting the interaction between CHFR and PARP1 with a small molecule. A3 inhibits the biochemical interaction between PARP1 and CHFR. 'A3' treatment leads to the functional disruption of the docataxel-induced mitotic checkpoint, a point in the cell cycle in which the CHFR-PARP1 interaction is greatest. 'A3' synergizes with docetaxel only in CHFR expressing cell lines. 'A3' administration results in a pharmacodynamic reduction in CHFR expression in vivo in human tumor xenograft models.

The invention claimed is:

1. A method of treating lung cancer comprising administering an effective amount of 5-((1-benzyl-1 H-indol-3 -yl) methylene)-1-(3,4- dimethylphenyl)pyrimidine-2,4,6(1H, 3H, 5H)-trione or salts thereof in combination with a taxane selected from paclitaxel and docetaxel to a subject in need thereof.

2. A method of treating breast cancer comprising administering an effective amount of 5-((1-benzyl-1 H-indol-3 -yl)methylene)-1-(3,4- dimethylphenyl)pyrimidine-2,4,6 (1H,3H, 5H)-trione or salts thereof in combination with a taxane selected from paclitaxel and docetaxel to a subject in need thereof.

3. A method of treating colon cancer comprising administering an effective amount of 5-((1-benzyl-1 H-indol- 3 -yl)methylene)-1-(3,4- dimethylphenyl)pyrimidine-2,4,6 (1H,3H, 5H)-trione or salts thereof in combination with a taxane selected from paclitaxel and docetaxel to a subject in need thereof.

4. The method of claim 3 further comprising administering a third anti-cancer agent.

5. The method of claim 4 wherein the third anti-cancer agent is selected from gefitinib, erlotinib, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and lenalidomide.

6. The method of claim 1 further comprising administering a third anti-cancer agent.

7. The method of claim 6 wherein the third anti-cancer agent is selected from gefitinib, erlotinib, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and lenalidomide.

8. The method of claim 2 further comprising administering a third anti-cancer agent.

9. The method of claim 8 wherein the third anti-cancer agent is selected from gefitinib, erlotinib, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin, mithramycin, etoposide, teniposide, amsacrine, topotecan, camptothecin, bortezomib, anagrelide, tamoxifen, toremifene, raloxifene, droloxifene, iodoxyfene, fulvestrant, bicalutamide, flutamide, nilutamide, cyproterone, goserelin, leuprorelin, buserelin, megestrol, anastrozole, letrozole, vorazole, exemestane, finasteride, marimastat, trastuzumab, cetuximab, dasatinib, imatinib, bevacizumab, combretastatin, thalidomide, and lenalidomide.

* * * * *